(12) United States Patent
Devi et al.

(10) Patent No.: US 6,855,807 B1
(45) Date of Patent: Feb. 15, 2005

(54) HETERODIMERIC OPIOID G-PROTEIN COUPLED RECEPTORS

(75) Inventors: Lakshmi Arehole Devi, New Rochelle, NY (US); Bryen Alexander Jordan, New York, NY (US)

(73) Assignee: New York University, New York, NY (US)

( * ) Notice: Subject to any disclaimer, the term of this patent is extended or adjusted under 35 U.S.C. 154(b) by 90 days.

(21) Appl. No.: 10/018,200

(22) PCT Filed: Jun. 15, 2000

(86) PCT No.: PCT/US00/16559

§ 371 (c)(1),
(2), (4) Date: Jan. 23, 2002

(87) PCT Pub. No.: WO00/77238

PCT Pub. Date: Dec. 21, 2000

Related U.S. Application Data

(60) Provisional application No. 60/139,528, filed on Jun. 16, 1999.

(51) Int. Cl.[7] .......................... C07K 1/00; C07K 14/00; C12N 15/74; G01N 33/53; C12P 21/06
(52) U.S. Cl. .................... 530/350; 435/7.2; 435/252.3; 435/325; 435/471; 435/69.1
(58) Field of Search .......................... 435/69.1, 252.3, 435/320.1, 471, 7.1, 7.2; 530/350, 402; 536/23.5

(56) References Cited

PUBLICATIONS

Egan TM and North RA. Science 214:923–924, 1981.*
Knapp et al. Molecular biology and pharmacology of cloned opiod receptors. FASEB J. Apr. 1995, vol. 9, pp. 516–525, see entire document, especially pp. 516–522 and Figures 4 and 5.
Sambrook et al. Molecular Cloning; a laboratory manual. 2nd ed. Cold Spring Harbor Press, 1989, pp. 17.2–17.44, see entire document.
Cvejic et al. Dimerization of the delta–opioid receptor: implication for a role in receptor internalization. J. biol. Chem., vol. 272. No. 43, pp. 26959–26964, 1997, see entire document.
Civelli et al. molecular Biology of the dopamine receptors. Eur. J. Pharmacol. 1991, vol. 207, pp. 277–286, especially pp. 278–280.
Ng, Gyc et al. Dopamine D2 receptor dimers and receptor–blocking peptides. Biochem. Biophys. Res. Comm. 1996, vol. 227, pp. 200–204.
Frielle et al. Properties of the B1– and B2–adrenergic receptor subtypes revealed by molecular cloning Clin. Chem. 1989, vol. 35, No. 5, pp. 721–725, see entire document.
Hebert et al. A peptide derived from b2–adrenergic receptor transmembrane domain inhibits both receptor dimerization and activation. 1996, vol. 271. No. 27, pp. 16384–16392, see entire document.
Power et al. Cloning and characterization of human chemokine receptors. Trends in Pharmacol. Sci. Jun. 1996, vol. 17, pp. 209–213, especillay Figure 2 and p. 212.
Rodriguez–Frade et al. The chemokine monocyte chemoattractant protein–1 induces functional responses through dimerization of its receptor CCR2. Mar. 1999, vol. 96, pp. 3628–3633, see entire document, especially Figure 1 and Figure 5.

* cited by examiner

*Primary Examiner*—Gary Kunz
*Assistant Examiner*—Robert Landsman
(74) *Attorney, Agent, or Firm*—Darby & Darby

(57) ABSTRACT

Opioid receptors form functional heterodimers with each other and with other G-protein coupled receptors, such as dopamine receptors, adrenergic receptors, or chemokine receptors. These receptors can be exploited for high throughput screening of compounds to identify heterodimer opioid receptor modulators (agonists and antagonists). The invention also relates to identification of novel heterodimer receptor ligands and synergistic compositions, which can provide strategies for analgesia, narcotic addiction, hypertension, HIV infection, and immune system function.

23 Claims, 16 Drawing Sheets

IP: Anti-Myc
IB: Anti-Flag

IB: Anti-Flag

IB: Anti-Flag

IP: Anti-Myc
IB: Anti-Flag

IP: HA-Ab
WB: C-Myc Ab

HETERODIMERIC OPIOID G-PROTEIN COUPLED RECEPTORS

This is the U.S. national phase application based upon International Application No. PCT/US00/16559 filed Jun. 15, 2000, and published in English on Dec. 21, 2000.

This application claims the benefit of priority under 35 U.S.C. §119 based upon U.S. Provisional Application Ser. No. 60/139,528 filed Jun. 16, 1999.

The entire disclosures of the prior applications are incorporated herein by reference.

The research leading to the present invention was supported, in part, by National Institute of Health Grants DA 08863 (National Institute of Drug Abuse) and NS1788 (National Institute of Neurological Diseases and Stroke). Thus, the United States Government has certain rights in the invention.

FIELD OF THE INVENTION

The present invention relates generally to opioid receptors, and more specifically to heterodimer opioid receptor, as well as to methods for identifying modulators (agonists and antagonists) of such receptors. The invention also relates to identification of novel heterodimer receptor ligands and synergistic compositions, which can provide strategies for analgesia, narcotic addiction, hypertension, and immune system function.

BACKGROUND OF THE INVENTION

The opioid system modulates several physiological processes including analgesia, stress response, immune response, and neuroendocrine function (Herz, *Opioids* Vol. 1, Springer-Verlag, Berlin, 1993). Pharmacological and molecular cloning studies have identified three opioid receptor types, delta ($\delta$), kappa ($\kappa$), and mu ($\mu$), that mediate these diverse effects (Miotto et al., The Pharmacology of Opioid Peptides, L. Tseng ed., 57–71, Harwood Acad. Publishers, 1995; Kieffer et al., Cell Mol. Neurobiol., 15:615–35, 1995). The opioid receptors are known to couple with pertussis toxin sensitive G-proteins.

Little is known, however, about the ability of these receptors to interact to form new functional structures, the simplest of which would be a dimer. Structural and biochemical studies reveal that other G-protein coupled receptors (GPCRs) interact to form homodimers (Herbert and Bouvier, Biochem Cell Biol., 76:1–11, 1998; Gouldson et al., Protein Eng., 11:1181–93, 1998). Moreover, non-functional GABA receptors heterodimerize to form a functional receptor, suggesting that dimerization is crucial for this receptor function (Jones et al., Nature, 396:674–679, 1998; Kaupmann, et al., Nature, 396:683–687, 1998; White et al., Nature, 396:679–682, 1998; and Kuner et al., Science, 283:7477, 1999).

It is now clear from work carried out in many laboratories over the last twenty years that there are three well-defined or "classical" types of opioid receptors: mu ($\mu$), delta ($\delta$), and kappa ($\kappa$). Genes encoding these receptors have been cloned (Evans et al., Science, 258:1952, 1992; Kieffer et al., Proc. Natl. Acad. Sci. USE, 89:12048, 1992; Chen et al., Mol. Pharmacol., 44:8, 1993; Minami et al., FEBS Lett., 329:291, 1993). More recently, cDNA was identified encoding an "orphan" receptor that has a high degree of homology to the "classical" opioid receptors; on the basis of its structural homology, this receptor has been classified as an opioid receptor and has been named ORL (opioid receptor-like) (Mollereau et al., FEBS Lett., 341:33, 1994). As would be predicted from their known abilities to couple through pertussis toxin-sensitive G-proteins, all of the cloned opioid receptors possess the same general structure of an extracellular N-terminal region, seven transmembrane domains and intracellular C-terminal tail structure. There is pharmacological evidence that subtypes of each receptor exist. Other types of novel, less well-characterized opioid receptors (termed $\epsilon, \gamma, \iota, \zeta$) have also been postulated. The $\sigma$-receptor, however, is no longer regarded as an opioid receptor.

Opioid receptors are reviewed extensively in a publication entitled "Opioid" edited by A. Herz and in a publication from Tocris Cookson Inc. (USA)/Tocris Cookson Ltd. (UK) entitled "Opioid Receptors", co-authored by A. Corbett, S. McKnight and G. Henderson, 1999.

$\mu$-Receptor Subtypes

The MOR-1 gene, encoding for one form of the $\mu$-receptor, shows approximately 50–70% homology to the genes encoding for the $\delta$-(DOR-1), $\kappa$-(KOR-1) and orphan (ORL$_1$) receptors. Two splice variants of the MOR-1 gene have been cloned, differing only in the presence or absence of 8 amino acids in the C-terminal tail. The splice variants exhibit differences in their rate of onset and recovery from agonist-induced internalization but their pharmacology does not appear to differ in ligand binding assays (Koch et al., N.S. Archives of Pharmacology, 357:SS44, 1998). Furthermore, in the MOR-1 knockout mouse, morphine does not induce antinociception, demonstrating that at least in this species morphine-induced analgesia is not mediated through $\delta$- or $\kappa$-receptors (Matthes et al., Nature, 383:818, 1996). Similarly morphine does not exhibit positive reinforcing properties or an ability to induce physical dependence in the absence of the MOR-1 gene. The $\mu_1/\mu_2$ subdivision was proposed by Pasternak and colleagues to explain their observations, made in radioligand binding studies, that $^3$H-labelled-$\mu$, -$\delta$, and -$\kappa$ ligands displayed biphasic binding characteristics (Wolozin and Pasternak, Proc. Natl. Acad. Sci. USA, 78:6181, 1981).

Several related observations suggest the existence of a yet unidentified form of $\mu$-receptor of which analogues of morphine with substitutions at the 6 position (e.g., morphine-6$\beta$-glucuronide, heroin and 6-acetyl morphine) are agonists, but with which unsubstituted morphine itself does not interact (Rossi et al., Neuroscience Letters, 216:1, 1996).

$\delta$-Receptor Subtypes

The DOR-1 gene is the only $\delta$-receptor gene cloned to date. However, two, overlapping subdivisions of $\delta$-receptor have been proposed ($\delta_1/\delta_2$ and $\delta_{cx}/\delta_{ncx}$) on the basis of in vivo and in vitro pharmacological experiments. The subdivision of the $\delta$-receptor into $\delta_1$ and $\delta_2$ subtypes was proposed primarily on the basis of in vivo pharmacological studies.

The $\delta_{cx}$ and $\delta_{ncx}$ subdivision of $\delta$-receptors was based on the hypothesis that one type of $\delta$-receptor ($\delta_{cx}$) was complexed with $\mu$-receptors (and perhaps also $\kappa$-receptors) whereas no association with an opioid receptor complex has been observed for the other type of $\delta$-receptor ($\delta_{ncx}$) (Rothman et al., *Handbook Exp. Pharmacol.*, A. Herz ed., 104/1:217, 1993).

Data obtained from subsequent radioligand binding studies have been interpreted as demonstrating the existence of further subtypes of the $\delta_{ncx}$ receptor, i.e., $\delta_{(ncx-1)}$ and $\delta_{(ncx-2)}$. More recently, it has been suggested that the $\delta_{(ncx-1)}$ receptor is in fact identical to the $\delta_1$-receptor and the $\delta_{cx}$-receptor is identical to the $\delta_2$-receptor of the previous classification (Xu et al., Peptides, 14:893, 1993).

$\kappa$-Receptor Subtypes

The situation regarding the proposals for subtypes of the $\kappa$-receptor is rather more complex than for the $\mu$- and δ-receptors, perhaps because of the continuing use of non-selective ligands to define the putative sites. The evidence for the need for sub-division of the κ-receptor comes almost entirely from radioligand binding assays.

Studies of $^3$H-ethylketocyclazocine $^3$H-EKC binding in guinea-pig spinal cord pointed to the existence of a non-homogeneous population of high-affinity binding sites, and led to the first proposal for $κ_1$- and $κ_2$-sites distinguished by their sensitivity to DADLE (Attali et al., Neuropeptides, 3:53, 1982).

Subdivision of the $κ_1$-site in guinea-pig brain into $κ_{1a}$ and $κ_{1b}$, was proposed to resolve the complex displacement of either $^3$H-EKC or $^3$H-U-69,593, with dynorphin B and α-neo-endorphin which both preferentially bound to the proposed $κ_{1b}$ sub-subtype (Clark et al., J. Pharmacol. Exp. Ther., 251:461, 1989). The same study proposed the existence of $κ_3$ subtype, insensitive to U-50,488, that was identified from the binding of $^3$H-naloxone benzoylhydrazone. The pharmacology of this later "$κ_3$-site" is rather different from the $κ_3$/MRF site of bovine adrenal medulla, and has been proposed to be the receptor mediating the antinociceptive effect of nalorphine, termed Martin's "N"-receptor (Paul et al., J. Pharmacol. Exp. Ther., 357:1, 1991).

Definitive functional pharmacological evidence supporting the existence of this confusing number of putative subtypes of the κ-receptor is lacking, because of the absence of subtype-specific antagonists.

All of this uncertainty and confusion about the precise identity of opioid receptors, and the number of different receptors, has hampered efforts to identify more effective, more specific opioid agonists and antagonists, i.e., more specific drugs with fewer untoward side effects, within a large family of neuropharmaceuticals including narcotic analgesics.

Thus, there is a need in the art to identify the molecular basis for the diversity of opioid receptor specificities.

There is a further need to identify specific opioid receptors for screening and development of more effective, less addictive, narcotics.

The present invention addresses these and other needs in the art.

SUMMARY OF THE INVENTION

The present invention relates to the discovery that opioid receptors form functional heterodimers. These receptors can be exploited for high-throughput screening of compounds to identify heterodimer opioid receptor modulators (agonists and antagonists). The invention also relates to identification of novel heterodimer receptor ligands and synergistic compositions, which can form the basis for therapeutic strategies to induce analgesia, to combat narcotic addiction, and to reduce hypertension, to name but a few such indications. Moreover, the discovery of certain of these receptor heterodimers has implications for improving immune system function.

The present invention provides an isolated heterodimeric receptor, which receptor comprises an opioid receptor subunit and a second G-protein coupled receptor (GPCR) subunit. Both receptor subunits are expressed endogenously in the same type of cell. Examples of such heterodimeric receptors include opioid-opioid receptor heterodimers, opioid-dopamine receptor heterodimers, and opioid-adrenergic receptor heterodimers. In specific embodiments, one or both of the receptors is a fusion protein comprising an epitope tag (i.e., a peptide segment that is recognized by an antibody).

The invention further provides a recombinant host cell that expresses a functional heterodimeric receptor, which receptor comprises an opioid receptor subunit expressed from an expression vector introduced into the host cell, and a second G-protein coupled receptor (GPCR) subunit expressed from an expression vector introduced into the host cell. Preferably, the host cell stably expresses both receptor subunits.

Also provided is a method of screening for a compound that modulates a property of a heterodimeric receptor as described above. This method comprises observing a change in a property of the heterodimeric receptor contacted with a candidate compound. For example, receptor trafficking, e.g., internalization, ligand binding, or ligand specificity can be altered in the presence of a test compound. In particular, heterodimeric opioid receptors will exhibit different affinity for various known and test ligands. In particular, the invention provides for testing the activity of bispecific, bivalent compounds discussed below, or synergistic compositions discussed below.

The invention also advantageously provides a bispecific, bivalent compound comprising an opioid receptor ligand bound to a second G-protein coupled receptor ligand, wherein the second receptor is expressed endogenously in a type of cell that also endogenously expresses the opioid receptor. Both ligands can be either agonists or antagonists of the specific receptor subunits that make up the heterodimer. Alternatively, antagonist/agonist combinations can provide for synergistic binding as well. For example, this is observed with kappa and delta heterodimeric receptor. In a specific embodiment, based on the surprising discovery made concerning covalent linkage of kappa receptor homodimers, both ligands of the compound are kappa receptor ligands.

In another aspect, the invention provides a pharmaceutical composition comprising synergistically effective amounts of a ligand of a delta opioid receptor and a ligand of a second receptor selected from the group consisting of kappa opioid receptor, mu opioid receptor, D2 dopamine receptor, and $β_2$-adrenergic receptor, and methods for identifying such compositions.

A pharmaceutical composition comprising synergistically effective amounts of a ligand of a kappa opioid receptor and a ligand of a second receptor selected from the group consisting of delta opioid receptor, D2 dopamine receptor, $β_2$-adrenergic receptor, $α_2$-adrenergic receptor, CCR5, and CXCR4.

A pharmaceutical composition comprising synergistically effective amounts of a ligand of a mu opioid receptor and a ligand of a second receptor selected from the group consisting of delta opioid receptor, and $α_2$-adrenergic receptor.

The compounds and compositions of the invention have heterodimeric opioid receptor modulating properties and thus therapeutic potential. These compounds address the need that exists for more precise identification of receptors for treating a disease or disorder of the central nervous system, cardiovascular system, or immune system. In particular, the disease or disorder may be chronic pain, drug abuse, schizophrenia, depression, or a dysfunction of the central reward pathway. The discovery of a kappa-CCR5 heterodimer provides an avenue for inhibiting HIV infection. The presence of heterodimeric receptors comprising an opioid receptor subunit and a catecholamine receptor subunit identifies a strategy for developing more effective treatments of cardiovascular disease, and in particular hypertension. Administering a therapeutically effective dose of a compound or a pharmaceutical composition of the invention is expected to have a therapeutic effect on such diseases and disorders.

DETAILED DESCRIPTION OF THE INVENTION

Figure 1A:
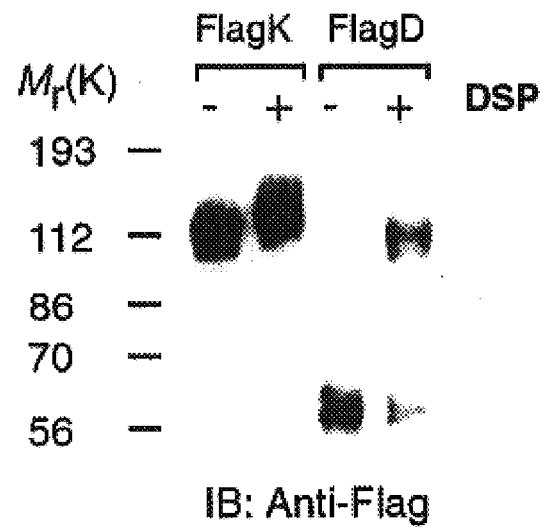
FIGS. 1A, B, C, D, and E. Characteristics of kappa opioid receptor homodimers. Immunoblotting of lysates from cells expressing FLAG-kappa receptors or FLAG-delta receptors (A). Myc-tagged kappa receptors can be co-precipitated only from cells expressing both myc and FLAG-tagged receptors (B) under a variety of extraction conditions and not from a mixture of cells individually expressing these receptors (C). Expression of myc- or FLAG-tagged receptors was confirmed by immunoblotting (right panel). Treatment of cells expressing kappa receptors with 1 mM DTT for 30 min followed by 5 mM IAM or NEM results in monomerization (D) whereas treatment with 100 nM agonists for 60 min does not (E).

For the first time, a heterodimeric receptor having at least one opioid receptor moiety or subunit has been characterized. The invetnion is based, in part, on biochemical and pharmacological evidence for the heterodimerization of fully functional opioid receptors (kappa and delta; and mu and delta), and fully functional opioid receptors/catecholamine receptors (delta and $β_2$-adrenergic receptor [$β_2$-AR]; kappa and D2; and delta and D2). Discovery of these receptors opens the door to the preparation of bispecific compounds and synergistic compositions of individual receptor ligands, based on the discovery of modified ligand specificity of these heterodimeric receptors and synergistic binding of receptor subunit-specific ligands. The present invention has uncovered the mechanism for synergy of different classes of drugs, which, though observed empirically, has not been satisfactorily explained until now. Thus, the present invention advantageously provides for the development both of more potent therapeutic agents and of a better understanding of the molecular basis of opioid receptor activity.

As used herein, the term "receptor subunit" refers to a single receptor protein that has been discovered to associate with another, different G-protein coupled receptor (GPCR), which is either a different opioid receptor protein or a non-opioid receptor, such as dopamine receptor, adrenergic receptor, or chemokine receptor. For example, in a kappa-delta opioid heterodimeric receptor, the kappa opioid receptor protein and the delta opioid receptor protein that form the heterodimer are each subunits.

The term "opioid receptor" refers to a "classical" type of opioid receptor: mu ($\mu$), delta ($\delta$), and kappa ($\kappa$). A "heterodimeric opioid receptor" or "opioid receptor heterodimer" refers to a G-protein coupled receptor of the invention, comprising an opioid receptor subunit and another GPCR receptor subunit, which maybe another opioid receptor subunit or a non-opioid receptor subunit.

Receptors are "expressed endogenously" in a type of cell that endogenously does or does not express the opioid receptor or are both expressed endogenously in the same type of cell (i.e., expressed together with a different opioid receptor(s) or a different GPCR [e.g., catecholamine receptor]). While such co-expression may have been recognized in the scientific literature, the discovery of the present invention represents the first indication that the receptor subunits form a functional heterodimer.

Non-limiting examples of endogenous co-expression of opioid receptors with other GPCRs include kappa and the D2 dopamine receptor; delta and D2; mu and delta; mu and $\alpha 2$-adrenergic receptor, delta and $\alpha_2$-adrenergic receptor, delta and $\beta_2$-adrenergic receptor, kappa and delta; kappa and $\beta_2$-adrenergic receptor; kappa and $ORL_1$ (nociceptin) receptor, delta and $ORL_1$ (nociceptin) receptor; and kappa and the CCR5 and CXCR4 chemokine receptors.

The term "functional" refers to the ability to accomplish at least one of the following: bind ligand; bind a "non-selective" ligand selectively; bind a bifunctional, bi-specific ligand; activate G-protein mediated signal transduction upon binding a ligand; induce internalization of the receptor; or any combination thereof. Such ability or abilities can be demonstrated in a cell based or cell-free system, or in vivo, including a transgenic animal system.

A bi-specific, bivalent compound of the invention comprises ligands for each of the individual heterodimeric receptor subunits bound to each other.

A "synergistically effective amount" of a ligand is an amount able to induce heterodimeric opioid receptor activity at a much lower concentration, particularly a subthreshold concentration, than is required for homodimeric (classical) receptor activity by virtue of the presence of a ligand of a different receptor, which is a subunit of the heterodimeric receptor. So, if ligand A is used, ligand B can be effective at a lower concentration than in the absence of A, and similarly when B is used, A can be effective at a lower concentration than in the absence of B. Although not intending to be bound by any particular explanation or theory, binding of one ligand to the heterodimeric receptor may alter conformation or otherwise facilitate recognition and binding of the other ligand. Thus, both ligands become surprisingly and unexpectedly effective at concentrations generally regarded as subthreshold (or subtherapeutic), even though the ligands themselves do not induce the same effects. Thus, any increase in efficacy represents a synergy, since there is no basis for expecting additive effects, e.g., with an opioid and a catecholamine.

Furthermore, the term "synergistic" can be used to describe an activity that two ligands have together that neither one has alone or in the absence of the other.

The term "signal transduction pathway" as used in this invention refers to the intracellular mechanism by which an opioid or other heterodimeric receptor ligand induces an alteration of cell function or activity. A key feature of the signal transduction pathway dissected herein is activation of G-protein coupled signaling, such as cAMP production, resulting in further signal transduction, including MAPK phosphorylation.

The term "element of a signal transduction pathway" refers to a signal transduction factor that is activated as a result of ligand binding to a heterodimeric receptor. In accordance with the present invention, elements of the signal transduction pathway include G-proteins, cAMP, MAPK, etc. A "signal" in such a pathway can refer to activation of an element (or factor) in the pathway. For example, activation of MAPK is a signal of agonist-induced kappa-delta heterodimer signal transduction pathway. Generally, activation of one of these factors involves phosphorylation of one or more proteins.

The term "inhibitor" is used herein to refer to a compound that can block or reduce the level of signaling in a signal transduction pathway described herein. Such an inhibitor may block the pathway at any point, from blocking binding of ligand to receptor to blocking function of intracellular signals. Preferably, an inhibitor discovered in accordance with the invention is specific for signals of heterodimeric opioid receptor-induced signalling.

"Screening" refers to a process of testing one or a plurality of compounds (including a library of compounds) for some activity. A "screen" is a test system for screening. Screens can be primary, i.e., an initial selection process, or secondary, e.g., to confirm that a compound selected in a primary screen (such as a binding assay) functions as desired (such as in a signal transduction assay). Screening permits the more rapid elimination of irrelevant or non-functional compounds, and thus selection of more relevant compounds for further testing and development. "High throughput screening" involves the automation and robotization of screening systems to rapidly screen a large number of compounds for a desired activity. Screens are discussed in greater detail below.

As used herein, the term "isolated" means that the referenced material is removed from its native environment, e.g., a cell. Thus, an isolated biological material can be free of some or all cellular components, i.e., components of the cells in which the native material occurs naturally (e.g., cytoplasmic or membrane component). A material shall be deemed isolated if it is present in a cell extract or if it is present in a heterologous cell or cell extract. In the case of nucleic acid molecules, an isolated nucleic acid fragment includes a PCR product, an isolated mRNA, a cDNA, or a restriction fragment. In another embodiment, an isolated nucleic acid fragment is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid fragment lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid fragment. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including without limitation preparative solid phase chromatography, oligonucleotide hybridization, and triple helix chromatography), ultracentrifugation, and other means. Polypeptides and proteins can be purified by various methods including, without limitation, preparative disc-gel electrophoresis and isoelectric focusing; affinity, HPLC, reversed-phase HPLC, gel filtration or size exclusion, ion exchange and partition chromatography; precipitation and salting-out chromatography; extraction; and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG, myc, HA, and GST. The polypeptide can then be purified from a crude lysate of the host cell by chromatography on an appropriate solid-pbase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible and contemplated herein. A purified material may contain less than about 50%, preferably less than about 75%, and most preferably less than about 90%, of the cellular components, media, proteins, or other nondesirable components or impurities (as context requires), with which it was originally associated. The term "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, logarithmic terms used in biology, the term "about" can mean within an order of magnitude of a given value, and preferably within one-half an order of magnitude of the value.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition, 1989, Cold Spring Harbor Laboratory Press, Cold Spring Harbor, N.Y. (herein "Sambrook et al., 1989"); DNA Cloning: *A Practical Approach*, Volumes I and II, D. N. Glover ed., 1985; *Oligonucleotide Synthesis*, M. J. Gait ed., 1984; *Nucleic Acid Hybridization*, B. D. Hames and S. J. Higgins eds., 1985; *Transcription And Translation*, B. D. Hames and S. J. Higgins, eds., 1984; *Animal Cell Culture*, R. I. Freshney ed., 1986; *Immobilized Cells And Enzymes*, IRL Press, 1986; B. Perbal, *A Practical Guide To Molecular Cloning*, 1984; *Current Protocols in Molecular Biology*, F. M. Ausubel et al. eds., John Wiley and Sons, Inc., 1994.

Molecular Biology—Definitions

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"). A "recombinant DNA molecule" is a DNA molecule that has undergone a molecular biological manipulation.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The coding sequences for individual receptors may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, intros, 5'- and 3'-non-coding regions, and the like.

The term "gene", also called a "structural gene" means a DNA sequence that codes for or corresponds to a particular sequence of amino acids which comprise all or part of one or more proteins, and may or may not include regulatory DNA sequences, such as promoter sequences, which determine for example the conditions under which the gene is expressed.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" or "operatively associated with" of transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracelular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme.

Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The term "expression system" means a host cell and compatible vector under suitable conditions, e.g., for the expression of a protein coded for by foreign DNA carried by the vector and introduced to the host cell. Expression systems include mammalian host cells and vectors. Suitable cells include PC12 cells, CHO cells, HeLa cells, 293 and 293T (human kidney cells), COS cells, mouse primary myoblasts, and NIH 3T3 cells.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, the opioid receptor gene and a second receptor gene are heterologous to the vector or vectors in which they are inserted for cloning or expression, and they are heterologous to a host cell containing such a vector, in which it is expressed, e.g., a CHO cell.

The terms "mutant" and "mutation" mean any detectable change in genetic material, e.g., DNA, or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position. Such variants can be used in expression of receptor subunits, e.g., where altered codon usage or insertion of a restriction site is desired.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable.

Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared. Any of these algorithms can be used with defaults provided by the manufacturer, supplier, or provider.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.)

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Equivalent stringency conditions can be achieved by increasing melting temperature and lowering salt concentration, or vica versa. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is a 0.1 5M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., 1989, supra, 9.50–9.51). For hybridization with shorter nucleic acids, i.e., oligonucleotides, the position of mismatches becomes more important, and the length of the oligonucleotide determines its specificity (see Sambrook et al., 1989, supra, 11.7–11.8).

A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, e.g., for cloning fill length or a fragment of a receptor. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Vectors

A wide variety of host/expression vector combinations may be employed in expressing DNA sequences encoding the heterodimeric opioid receptor subunits. Useful expression vectors, for example, may consist of segments of chromosomal, non-chromosomal and synthetic DNA sequences. Suitable vectors include SV40 and derivatives of SV40 and bacterial plasmids, e.g., E. coli plasmids col E1, pCR1, pBR322, pMal-C2, pET, pGEX (Smith et al., Gene, 67:31–1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2 m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

A vector can be introduced in vivo in a non-viral vector, e.g., by lipofection, with other transfection facilitating agents (peptides, polymers, etc.), or as naked DNA. Synthetic cationic lipids can be used to prepare liposomes for in vivo transfection, with targeting in some instances (Felgner, et. al., Proc. Natl. Acad. Sci. USA, 84:7413–7417, 1987; Felgner and Ringold, Science, 337:387–388, 1989; Mackey, et al., Proc. Natl. Acad. Sci. USA, 85:8027–8031, 1988; Ulmer et al., Science, 259:1745–1748, 1993). Useful lipid compounds and compositions for transfer of nucleic acids are described in PCT Publication Nos. WO 95/18863 and WO 96/17823, and in U.S. Pat. No. 5,459,127. Other molecules are also useful for facilitating transfection of a nucleic acid in vivo, such as a cationic oligopeptide (e.g., PCT Publication No. WO 95/21931), peptides derived from DNA binding proteins (e.g., PCT Publication No. WO 96/25508), or a cationic polymer (e.g., PCT Publication No.

WO 95/21931). Recently, a relatively low voltage, high efficiency in vivo DNA transfer technique, termed electrotransfer, has been described (Mir et al., C.P. Acad. Sci., 321:893, 1998; PCT Publications Nos. WO 99/01157; WO 99/01158; WO 99/01175). DNA vectors for gene therapy can be introduced into the desired host cells by methods known in the art, e.g., electroporation, microinjection, cell fusion, DEAE dextran, calcium phosphate precipitation, use of a gene gun (ballistic transfection), or use of a DNA vector transporter (see, e.g., Wu et al., J. Biol. Chem., 267:963–967, 1992; Wu and Wu, J. Biol. Chem., 263:14621–14624, 1988; Canadian Patent Application No. 2,012,311; Williams et al., Proc. Natl. Acad. Sci. USA, 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987). U.S. Pat. Nos. 5,580,859 and 5,589,466 disclose delivery of exogenous DNA sequences, free of transfection facilitating agents, in a mammal.

Also useful are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional protein or polypeptide (as set forth above) can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication No. WO 95/28494.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci., 2:320–330, 1991), defective herpes virus vector lacking a glyco-protein L gene (Patent Publication RD 371005 A), or other defective herpes virus vectors (PCT Publication Nos. WO 94/21807 and WO 92/05263); an attenuated adenovirus vector, such as the vector described by Stratford-Perricaudet et al. (J. Clin. Invest., 90:626–630, 1992; see also La Salle et al., Science, 259:988–990, 1993); and a defective adeno-associated virus vector (Samulski et al., J. Virol., 61:3096–3101, 1987; Samulski et al., J. Virol., 63:3822–3828, 1989; Lebkowski et al., Mol. Cell. Biol., 8:3988–3996, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

A preferred expression host is a eukaryotic cell (e.g., yeast, insect, or mammalian cell). More preferred is a mammalian cell, e.g., human, rat, monkey, dog, or hamster cell. In specific embodiments, infra, opioid receptor heterodimers are expressed in a human embryonic kidney (HEK) 293 line or a COS line. Other choices include a cell line (e.g., SK-N-MC), or a chinese hamster ovary cell line (e.g., CHO-K1).

Expression of one or both receptor subunits may be controlled by any promoter/enhancer element known in the art, but these regulatory elements must be functional in the host selected for expression. Promoters which may be used for gene expression include, but are not limited to, cytomegalovirus (CMV) promoter (U.S. Pat. Nos. 5,385,839 and 5,168,062), the SV40 early promoter region (Benoist and Chambon, 1981, Nature, 290:304–310), the promoter contained in the 3' long terminal repeat of Rous sarcoma virus (Yamamoto et al., Cell, 22:787–797, 1980), the herpes thymidine kinase promoter (Wagner et al., Proc. Natl. Acad. Sci. USA, 78:1441–1445, 1981), the regulatory sequences of the metallothionein gene (Brinster et al., Nature, 296:39–42, 1982); prokaryotic expression vectors such as the β-lactamase promoter (Villa-Kamaroffet al., Proc. Natl. Acad. Sci. USA, 75:3727–3731, 1978), or the tac promoter (DeBoer et al., Proc. Natl. Acad. Sci. USA, 80:21–25, 1983); see also "Useful proteins from recombinant bacteria" in Scientific American, 242:74–94, 1980; promoter elements from yeast or other fungi such as the Gal4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., Cell 38:639–646, 1984; Ornitz et al., Cold Spring Harbor Symp. Quant. Biol., 50:399–409, 1986; MacDonald, Hepatology, 7:425–515, 1987); insulin gene control region which is active in pancreatic beta cells (Hanahan, Nature, 315:115–122, 1985), immunoglobulin gene control region which is active in lymphoid cells (Grosschedl et al., Cell, 38:647–658, 1984; Adames et al., Nature, 318:533–538, 1985; Alexander et al., Mol. Cell. Biol., 7:1436–1444, 1987), mouse mammary tumor virus control region which is active in testicular, breast, lymphoid and mast cells (Leder et al., Cell, 45:485–495, 1986), albumin gene control region which is active in liver (Pinkert et al., Genes and Devel., 1:268–276, 1987), alpha-fetoprotein gene control region which is active in liver (Krumlauf et al., Mol. Cell. Biol., 5:1639–1648, 1985; Hammer al., Science, 235:53–58, 1987), alpha 1-antitrypsin gene control region which is active in the liver (Kelsey et al., *Genes and Devel.*, 1:161–171, 1987), beta-globin gene control region which is active in myeloid cells (Mogram et al., Nature, 315:338–340, 1985; Kollias et al., Cell, 46:89–94, 1986), myelin basic protein gene control region which is active in oligodendrocyte cells in the brain (Readhead et al., Cell, 48:703–712, 1987), myosin light chain-2 gene control region which is active in skeletal muscle (Sani, Nature, 314:283–286, 1985), and gonadotropic releasing hormone gene control region which is active in the hypothalamus (Mason et al., Science, 234:1372–1378, 1986).

Specific Receptor Combinations

Various heterodimeric receptor combinations, based on endogenous co-expression of the receptor subunits, are specifically contemplated by the invention. Specific examples are set forth below. In these instances, the existence of a heterodimeric receptor form accounts for the observed characteristics of ligand binding. Thus, in the section that follows, the boldface headings are contributed by the present invention. The explanatory text explains the basis for identification of the heterodimeric receptor of the invention based on evidence for co-expression of each receptor subunit in the cell, and in some instances by previously unexplained pharmacological data.

The identification of these specific receptor combinations provides a basis for identify heterodimeric receptor ligands that modulate cellular activity. Modulation of the heterodimeric receptor combinations with such ligands will provide a strategy for affecting various neurological and physiological changes in vivo.

It bears noting that although the following receptors have been identified as co-expressed in cells, and in some cases there is evidence for co-modulation of ligand binding, there is no indication of the possible existence of a heterodimeric opioid receptor of the invention.

Kappa and D2:

The noradrenergic neurons of the autonomic nervous and the central nervous system are endowed with presynaptic receptors by which noradrenaline release is inhibited by noradrenaline itself (via the $\alpha_2$-autoreceptor) and by other transmitters and mediators (via heteroreceptors). Frequently, inhibitory interactions exist between auto- and heteroreceptors, as is the case for the following heteroreceptors: adenosine A1, cannabinoid CB1, dopamine D2/D3, histamine H3, 5-hydroxytryptamine (seratonin) 5-HT (1B), imidazoline muscarine M2, delta opioid, kappa opioid, mu opioid, orphan opioid (ORL1), prostaglandin EP3 and somatostatin SRIF1. Such interactions May prevent the identification of a putative heteroreceptor or the quantitative estimation of the effect mediated by this receptor (Schlicker and Gothert, Brain Res. Bull., 47:129, 1998).

Studies on rats, where U-69593, the selective κ-opioid agonist, was repeatedly administered in daily injections, demonstrated that kappa-opioid agonists induce long-term alterations in dopamine D2 receptors. Furthermore, the finding that these changes in receptor number require repeated injections and a withdrawal time of one day suggests that these alterations are compensatory in nature (Izenwasser et al., Synapse, 30:275, 1998).

The presynaptic regulation of stimulated dopamine release from superfused rat striatal synaptosomes by opioids and GABA has been studied. It was found that dopamine D2 autoreceptors were inhibited through activation of a homogenous population of kappa-opioid receptors in view of the potent inhibitory effect of kappa-selective agonist U-69593 (Ronken et al., J Neurochem., 61:1634, 1993).

The present invention provides the first biochemical and pharmacological evidence for the heterodimerization of the fully functional kappa opioid receptor and the dopamine D2 receptor. As described in more detail in the Example 3 (infra), this heterodimerization was demonstrated using co-expression of the tagged versions of the two receptors in cultured cells (that normally don't express these receptors), followed by immunoprecipitation of receptor heterodimers with anti-tag antibodies. Kappa-dopamine D2 heterodimers were observed only in lysate from cells co-expressing the two receptors together, and not in the lysate from a mixture of cells individually expressing these receptors. From ligand binding studies it was also shown that, when administerd together, highly selective ligands of the two receptors (agonists or antagonists) bound co-operatively and synergistically potentiated the hetero-receptor function.

Kappa and $\beta_2$:

The present invention also provides the first biochemical and pharmacological evidence for the heterodimerization of the fully functional kappa opioid receptor and the $\beta_2$-adrenergic receptor. The experimental approach was identical to the one employed for kappa-dopamine D2 heterodimers, and is described in more detail in the Example 3 (infra).

Kappa and Delta:

According to the present invention the ability of kappa receptors to heterodimerize with delta receptors was shown by co-expressing myc-tagged kappa receptors with FLAG-tagged delta receptors in cultured cells, followed by immunoprecipitation using antibodies specific for myc-tagged kappa receptors (described in more detail in the Example 1, infra). It was also shown that kappa-delta heterodimers are destabilized by a reducing agent indicating that disulfide bonds are involved in kappa-delta heterodimerization.

The present invention also addressed the issue of functional significance of kappa-delta heterodimerization. Thus, the pronounced effect of heterodimerization on receptor trafficking (i.e., internalization) was demonstrated using cells co-expressing kappa and delta receptors and etorphine, a potent non-selective opioid agonist that binds both delta and kappa receptors with high affinity. In addition, the results of ligand binding/competition assays imply that kappa-delta heterodimerization produces a new binding site which is able to synergistically bind highly selective ligands. The synergistic activation of heterodimeric receptor by selective ligands is reflected in a significant potentiation of signal transduction pathways (e.g., cAMP level reduction, activation of MAPK), and suggests that the kappa-delta heterodimer represents a functional receptor with novel properties.

Delta and D2:

Co-expression of these receptors was reported in, inter alia, Fuxe et al., *The Opioid Peptide Systems: Their Organization and Role in Volume Transmission and Neuroendocrine Regulation. In: Regulatory Roles of opioid Peptides*, Illes, P., Farsang, C Weinham eds., New York, pp 33–68, 1988. The present invention provides the first biochemical and pharmacological evidence for the heterodimerization of the fully functional delta opioid receptor and the dopamine D2 receptor. The experimental approach was identical to the one employed for kappa-dopamine D2 heterodimers (supra), and is described in more detail in the Example 3 (infra).

Mu and Delta:

Dopamine D1 receptor-stimulated cyclic AMP efflux from superfused neostriatal slices was strongly inhibited by the delta-opioid receptor agonist [D-Pen2, D-Pen5] enkephalin (DPDPE, 1 μM) and by the mu-opioid receptor agonist [D-Ala2, MePhe4, Gly-ol5] enkephalin (DAGO, 1 μM). The data indicate that FIT (fentanyl isothiocyanate) and Naloxone, acting on delta and mu receptors, respectively, may share a common binding site (Schoffelmeer et al., Eur. J. Pharmacol., 149:179, 1988), suggesting the involvement of a functional mu-delta opioid receptor complex.

Previous studies delineated two classes of delta binding sites; a delta not associated with the opioid receptor complex, termed the delta ncx site, and a delta site associated with the opioid receptor complex, termed the delta cx site. The main findings were that the pretreatment of membranes with (+)-trans-SUPERFIT, a delta selective acylating agent, decreased the IC50 values (i.e., concentration required for 50% inhibition of binding) of delta-preferring drugs, and increased the IC50 values of mu-preferring drugs, for the delta cx binding site. Mu preferring drugs were non-competitive inhibitors of $^3$H[D-Ala, Leu5] enkephalin binding to the delta cx site, delta-preferring drugs were competitive inhibitors (Rothman et al., Pepbides, 13:1137, 1992).

Acute antinociceptive effects of opioid mu agonists were shown to be modulated by delta agonists, while the development of antinociceptive tolerance was not (Jiang et al., Eur. J. Pharmacol., 186:137, 1990).

Radioligand binding assays and functional experiments revealed that the SK-N-BE neuroblastoma cell line expresses a similar ratio of mu and delta opioid receptors, both negatively coupled to adenylyl cyclase through pertussis toxin-sensitive G-proteins (Palazzi et al., J. Neurochem., 67:138, 1996). The findings here indicate that some functional interaction occurred between the two opioid subtypes. In fact, a long term exposure to DAMGO, a mu-selective agonist, sensitized the functional response of the delta-selective agonist, but not vice versa. These data supports the hypothesis of the existence of cross-talk between mu and delta receptors in the SK-N-BE cell line.

Morphine is known to bind primarily to mu receptors; this is supported by the total lack of response to morphine in transgenic animals lacking mu opioid receptors (Mathes et al., Nature, 383:819–823, 1996). Interestingly, in these animals the delta ligand-mediated analgesia is also altered suggesting an interaction between these two receptors (Sora et al., Eur J. Pharmacol., R1–R29, 1997). Likewise, in wild-type animals chronic morphine treatment was found to selectively upregulate a subpopulation of delta opioid receptors (Rothman et al., Eur. J. Pharm., 160:71–82, 1989; Rothman et al., Eur. J. Pharm., 124:113–119, 1986). When opioid receptor roles in the analgesia were assessed using classical delta-opioid receptor agonist, DPDPE, analgesia was dramatically reduced in mu-opioid receptor knockout mice in a gene-dose dependent fashion (Sora et al., supra).

In addition, immunohistochemical studies of the opioid receptor distribution in the CNS have shown that mu and delta receptors co-localize to the same axonal terminals of the superficial dorsal horn (Mohler and Fritschy, Trends in Pharmacol. Sci., 20:87–89, 1999; Vaught et al., Life Sci., 30:1443–1445, 1982).

As detailed in Example 2 (infra), the present invention describes the isolation (by immunoprecipitation) of approximately 150 kDa mu-delta heterodimer from the cultured cells expressing both receptors in their tagged forms. Examination of the ligand binding properties of the mu-delta heterodimer in cells expressing both receptors revealed the synergistic binding of receptor type selective ligands suggesting the formation of a heterodimer-specific novel binding site. Morphine and other opiates were demonstrated to bind this site with super high affinity.

Mu and $\alpha_2$:

Mu-opioid receptor efficacy appears to be dependent on the degree of activation of $\alpha_2$-adrenoceptors in central noradrenergic nerve terminals, possibly through a local receptor interaction within the nerve terminal membrane (Schoffelmeer et al., N. S. Arch. Pharmacol., 333:377, 1986).

In pontine slices of the rat brain, the frequency of the spontaneous action potentials of locus coeruleus (LC) neurons was recorded extracellularly. The spontaneous activity of LC neurons was inhibited by somatic alpha 2-adenoceptors and opioid mu-receptors. It has been suggested that the two receptors interact with each other at a site located between themselves and not in the subsequent common signal transduction system (Illes and Norenberg, N. S. Arch Pharmacol., 342:490, 1990).

A number of in vivo studies have shown that $\alpha_2$-adrenergic receptor modulates opioid effects (Aley and Levine, J. Neurosci., 17:735–744, 1997; Bentley et al., Br. J. Pharmacol., 79:125–134, 1983; Bucher et al., N. S. Arch Pharmacol., 345:37–43, 1992; Stone et al., J Neurosci., 17:7157–65, 1997). One of these studies (Aley and Levine, supra) showed that morphine was able to modulate the activity of $\alpha_2$-adrenergic receptor and not of the A1 adenosine receptor. This receptor cross talk is hypothesized to be either via second messenger systems or via physical association of the receptors. However, the asymmetric interactions as observed by morphine's ability to modulate the activity of $\alpha_2$C-adrenergic receptor and not of the A1 adenosine receptor, although both receptors negatively coupled to adenylate cyclase, has led to the proposal that the receptors are physically associated on the membranes and that the mu receptors have the ability to complex with $\alpha_2$C-adrenergic receptor and not with the A1 adenosine receptor (Darland and Grandy, Br. J. Anaesth., 81:29–37, 1998 ). In support of this, studies carried out by Stone et al. (supra) have shown that the $\alpha_2$A-adrenergic receptor subtype (a point mutation in the $\alpha_2$A-adrenergic receptor) is the primary mediator of $\alpha_2$A-adrenergic spinal analgesia and is necessary for analgesic synergy with opioids. This synergy between opiates and adrenergic drugs in mediating spinal analgesia is lost in transgenic animals lacking functional adrenergic receptor. The present invention provides the first biochemical and pharmacological evidence for the heterodimerization of the fully functional delta opioid receptor and $\alpha_2$A-adrenergic receptor. The experimental approach was identical to the one employed in kappa-$D_2$ heterodimers, and is described in detail in Example 3 (infra).

Kappa and $\alpha_2$:

The interaction of presynaptic, release inhibiting alpha 2-adrenoceptors, opioid kappa-receptors and adenosine $A_1$-receptors was studied in slices of the parieto-occipital cortex of rabbits. The selective kappa-receptor agonist ethylketocyclazocine (EK) attenuated markedly the release-inhibiting effects of the $\alpha_2$-adrenoceptor-selective agonists and antagonists (Limberger et al., N. S. Arch Pharmacol 338:53, 1988). It was concluded that there is an interaction between presynaptic $\alpha_2$-adrenoceptors and opioid kappa-receptors, either at the level of the receptors themselves or of the post-receptor reaction chains.

Delta and $\beta_2$:

Cardiac myocyte sarcolemma contains both catecholamine and opioid peptide receptors (OPRs). Potent inhibitory "cross-talk" between delta-OPR and $\beta$-adrenergic receptor signaling pathways was found to occur via a PTX (pertussis toxin) sensitive G-protein involved in adenylyl cyclase inhibition in rat heart (Pepe et al., Circulation, 95:2122, 1997), suggesting the interaction between delta-OPR and β-adrenergic receptor.

The present invention provides the first biochemical and pharmacological evidence for the heterodimerization of the fully functional delta opioid receptor and the $β_2$-adrenergic receptor. The experimental approach was identical to the one employed for kappa-dopamine D2 heterodimers (supra), and is described in more detail in the Example 3 (infra).

Kappa and CCR5 or CXCR4:

Co-expression of these receptor types has been previously reported (Chao et al., Proc. Natl. Acad. Sci. USA, 923:8051–6, 1996). The isolation of opioid receptor dimers with other opioid, dopamine, and adrenergic receptors, which is disclosed in the present invention, suggests the possibility of formation of kappa-CCR5 and kappa-CXCR4 heterodimers. Given the approaches disclosed in the present invention, anyone skilled in the art would be in the position to demonstrate the existence of kappa-CCR5 and kappa-CXCR4 heterodimers experimentally. The existence of such heterodimers will, in turn, explain a previously reported feedback of opiates on immune system function. It will also provide a solid basis for using opioids as competitors for undesirable chemokine receptor interactions. Primary among these undesirable interactions is the interaction of HIV with CCR5 for intracellular transport.

Opioid Receptor and Nociceptin Receptor:

Another candidate for heterodimerization with opioid receptors is a recently identified nociceptin receptor. The cDNA for nociceptin (also designated orphanin FQ) receptor was isolated based on the homology to opioid receptors (Civelli et al., Crit. Rev. Neurobiol., 12,163–76, 1998). A search for ligands that activate this receptor led to the identification of nociceptin (orphanin FQ) peptides (Darland and Grandy, supra). Pharmacological and behavioral studies have shown that these peptides modulate opiate-mediated analgesia (Civelli et al., supra).

Screening Assays

As exemplified in the Examples, infra, the present invention provides various screening assays for modulation of heterodimeric opioid receptor activation. The assays of the invention are particularly advantageous by permitting rapid evaluation of cellular responses. Biological assays, which depend on testing perception, pain sensitivity, survival, or some other response in vivo require substantial amounts of time and resources to evaluate. By detecting individual signals in the signal transduction pathway, the present invention short-circuits the more tedious and time consuming biological assays. Furthermore, the signal transduction assays can often be performed with very small amounts of material.

In general, a screening assay of the invention makes use of the cells expressing receptor proteins (described above), various heterodimeric receptor ligands, and a candidate compound for testing.

The present invention contemplates screens for small molecule compounds, including peptides and peptidomimetics, and including receptor ligand analogs and mimics, as well as screens for natural compounds that bind to and agonize or antagonize heterodimeric opioid receptors in vito. Such agonists or antagonists may, for example, interfere in the phosphorylation or dephosphorylation of signal transduction proteins. For example, natural products libraries can be screened using assays of the invention for such molecules. As used herein, the term "compound" refers to any molecule or complex of more than one molecule that modulates heterodimeric opioid receptor function. The present invention contemplates screens for synthetic small molecule agents, chemical compounds, chemical complexes, and salts thereof as well as screens for natural products, such as plant extracts or materials obtained from fermentation broths. Other molecules that can be identified using the screens of the invention include opioids, opiates, narcotics, proteins and peptide fragments, peptides, nucleic acids and oligonucleotides, carbohydrates, phospholipids and other lipid derivatives, steroids and steroid derivatives, prostaglandins and related arachadonic acid derivatives, etc.

One approach to identifying such compounds uses recombinant bacteriophage to produce large libraries. Using the "phage method" (Scott and Smith, Science, 249:386–390, 1990; Cwirla, et al., Proc. Natl. Acad. Sci.USA, 87:6378–6382, 1990; Devlin et al., Science, 49:404–406, 1990), very large libraries can be constructed ($10^6$–$10^8$ chemical entities). A second approach uses primarily chemical methods, of which the Geysen method (Geysen et al., Molecular Immunology, 23:709–715, 1986; Geysen et al., J. Immunologic Method, 102:259–274, 1987) and the method of Fodor et al. (Science, 251:767–773, 1991) are examples. Furka et al. (14th *International Congress of Biochemistry*, Volume 5, Abstract FR:013, 1988; Furka, Int J. Peptide Protein Res., 37:487–493, 1991) and U.S. Pat. Nos. 4,631,211 and 5,010,175 describe methods to produce a mixture of peptides that can be tested as agonists or antagonists.

In another aspect, synthetic combinatorial libraries (Needels et al., Proc. Natl. Acad. Sci. USA, 90:10700–4, 1993; Ohlmeyer et al., Proc. Natl. Acad. Sci. USA, 90:10922–10926, 1993; PCT Publication Nos. WO 92/00252 and WO 94/28028) and the like can be used to screen for compounds according to the present invention.

Test compounds may be screened from large libraries of synthetic or natural compounds. Numerous means are currently used for random and directed synthesis of saccharide-, peptide-, and nucleic acid-based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal tracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., Tib Tech, 14:60, 1996).

In one embodiment, test compounds are peptides or peptidomimetic compounds generated by rational drug design based on the structure of known opioid peptides, or derived from combinatorial libraries. The term "peptide" is used in its broadest sense to refer to a compound of two or more subunit amino acids, amino acid analogs or peptidomimetics. The subunits may be linked by peptide bonds. In another embodiment, the subunits may be linked by other bonds, e.g., ester, ether, etc. As used herein the term "amino acid" refers to either natural and/or unnatural or synthetic amino acids, including glycine and both the D or L optical isomers, and amino acid analogs and peptidomimetics. Thus, peptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties to peptides in the library.

Additionally, by assigning specific amino acids at specific coupling steps, peptide libraries with α-helices, β-turns, β-sheets, γ-turns, and cyclic peptides can be generated. A peptide of three or more amino acids is commonly called an oligopeptide if the peptide chain is short. If the peptide chain is long, the peptide is commonly called a polypeptide or a protein.

The following non-classical amino acids may be incorporated in peptyides of the invention to introduce particular conformational motifs: 1,2,3,4-tetrahydroisoquinoline-3-carboxylate (Kazmierski et al., 1991, J. Am. Chem. Soc., 113:2275–2283); (2S,3S)-methyl-phenylalanine, (2S,3R)-methyl-phenylalanine, (2R,3S)-methyl-phenylalanine and (2R,3R)methyl-phenylalanine; 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs, 43:53–76); b-carboline (D and L) (Kazmierski, 1988, Ph.D. Thesis, University of Arizona); histidine isoquinoline carboxylic acid, HIC (Zechel et al., 1991, Int. J. Pep. Protein Res., 38:131–138); and histidine cyclic urea (Dharanipragada). The following amino acid analogs and peptidomimetics may be incorporated to induce or favor specific secondary structures: LL-Acp (LL-3-amino-2-propenidone-6-carboxylic acid), a β-turn inducing dipeptide analog (Kemp et al., 1985, J. Org. Chem., 50:5834–5838); β-sheet inducing analogs (Kemp et al., 1988, Tetrahedron Lett. 29:5081–5082); β-turn inducing analogs (Kemp et al., 1988, Tetrahedron Lett., 29:5057–5060); $\mu$-helix inducing analogs (Kemp et al., 1988, Tetrahedron Lett., 29:4935–4938); γ-turn inducing analogs (Kemp et al., 1989, J. Org. Chem., 54:109:115); and analogs provided by the following references: Nagai and Sato, 1985, Tetrahedron Lett., 26:647–650; DiMaio et al., 1989, J. Chem. Soc. Perkin Trans., p. 1687; also a Gly-Ala turn analog (Kahn et al., 1989, Tetrahedron Lett., 30:2317); amide bond isostere (Jones et al., 1988, Tetrahedron Lett., 29:3853–3856); tretrazol (Zabrocki et al., 1988, J. Am. Chem. Soc., 110:5875–5880); DTC (Samanen et al., 1990, Int. J. Protein Pep. Res., 35:501:509); and analogs taught in Olson et al., 1990, J. Am. Chem. Sci., 112:323–333 and Garvey et al., 1990,J. Org. Chem., 56:436.

The coupling of the amino acids may be accomplished by techniques familiar to those in the art (Stewart and Young, 1984, *Solid Phase Synthesis*, Second Edition, Pierce Chemical Co., Rockford, Ill.; Fields and Noble, 1990, Int. J. Pept. Protein Res., 35:161–214), or using automated synthesizers, such as sold by ABS.

Intact cells expressing heterodimer of interest can be used in screening methods to identify candidate drugs. In one series of embodiments, a permanent cell line is established, e.g., as exemplified below. Alternatively, cells (including without limitation mammalian, insect, yeast, or bacterial cells) are transiently programmed to express the receptor subunit genes by introduction of appropriate DNA or mRNA. Identification of candidate compounds can be achieved using any suitable assay, including without limitation (i) assays that measure selective binding of test compounds; (ii) assays that measure the ability of a test compound to modify (i.e., inhibit or enhance) a measurable activity or function of the receptor; (iii) assays that monitor receptor trafficking, e.g., internalization and re-expression; and (iv) assays that measure the ability of a compound to modify (i.e., inhibit or enhance) transcription of proteins induced by the receptor.

High-Throughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (e.g., using a 96-well format). For literature references see, e.g., Beggs et al., 1999, J. Biol. Screening, Vol.4, No.3; Renate de Wit et al., 1998, J. Biol. Screening, Vol.3, No.4; Fox et al., 1999, J. Biol. Screening, Vol.4, No.4; Boyd et al., 1996, Clin.Chem., 42:1901–10; Broach et al., 1996, Nature, 384, Supp.:14–16; Cusack et al., 1993, J. Rec. Res., 13:123–134; U.S. Pat. Nos. 4,980,281 and 5,876,951; PCT Publication Nos. WO 97/45730, WO 97/14812, and WO 97/10502. Such high-throughput screening methods are particularly preferred. The use of high-throughput screening assays to test for agents is greatly facilitated by the availability of large amounts of purified polypeptides, as provided by the invention.

Specific Screening Methods

There are several screening methods available for the discovery of specific heterodimer receptor ligands. These screens include radioligand binding, signal transduction, expression, reporter assays, and structure function of existing agonists and antagonists. The utilization of yeast as a screening tool can accelerate the search for novel opioid analogs. This technology can be utilized for screening of novel compounds that are identified in high throughput screens.

Radioligand Binding Assays

Radioligand binding assays allow further characterization of hits from high throughput screens as well as analogs of heterdimer receptor agonists and antagonists. Any of the ligands described below can be radiolabelled for direct binding assays, or alternatively, used in competitive binding assays.

Signal Transduction Assays

G protein coupled receptors (GPCR) are coupled to a variety of heterotrimeric G proteins, which are comprised of α, β, and γ subunits. Upon agonist binding to a GPCR at the cell surface, conformational changes occur within the agonist:GPCR complex, which lead to the dissociation of the G protein a subunit from the βγ subunits. The $G_\alpha$ and $G_{\beta\gamma}$ subunits then stimulate a variety of intracellular effectors, which transduce the extracellular signal to the inside of the cell. Various signal trnsduction systems known to be coupled to GPCRs include adenylate cyclase, phospholipase C, phospholipase $A_2$, sodium/hydrogen exchange, etc. Thus, measurements of intracellular calcium concentrations and adenylate cyclase activity indicate whether a hit or test compound is functionally behaving as an agonist or antagonist at the heterodimeric receptor of the invention.

In a specific embodiment, G-protein signal transduction is coupled to expression of a reporter gene, thus permitting a reporter gene screening assay.

Calcium Mobilization Assay

Whole cells expressing the heterodimeric receptor are loaded with a fluorescent dye that chelates calcium ions, such as FURA-2. Upon addition of receptor agonist to these cells, calcium is released from the intracellular stores. The dye chelates these calcium ions. The spectrophotometrically determined ratio of the dye:calcium complexes to free dye provides a numerical measurement of the changes in intracellular calcium concentrations upon addition of opioid-like substrate. Hits from screens and other test compounds can be similarly tested in this assay to functionally characterize them as agonists or antagonists. Increases in intracellular calcium concentrations are expected for compounds with agonist activity while compounds with antagonist activity are expected to block opioid-like substrate stimulated increases in intracellular calcium concentrations.

Cyclic AMP Accumulation Assay

Upon agonist binding, $G_s$-coupled GPCRs stimulate adenylate cyclase. Adenylate cyclase catalyzes the production of cyclic AMP (cAMP) from adenosine-5'-triphosphate which, in turn, activates protein kinases. $G_i$-coupled GPCRs are also coupled to adenylate cyclase, however, agonist binding to these receptors results in the inhibition of adenylate cyclase and the subsequent inhibition of cAMP accumulation. To measure the inhibition of cAMP accumulation, cells expressing $G_i$-coupled receptors must first be stimulated to elevate cAMP levels. This is achieved by treating the cells with forskolin, a diterpene that directly stimulates cAMP production. Co-incubation of cells expressing $G_i$-coupled receptors with forskolin and a functional agonist will result in the inhibition of forskolin-stimulated cAMP accumulation. For a cAMP assay, cells stably expressing a heterodimeric receptor of the invention can be incubated with a test compound, and with forskolin plus a test compound. The cells are then lysed and cAMP levels are measured using the [$^{125}$I]cAMP radioimmunoassay (RIA).

Methods for Detecting Signals

The present invention provides numerous methods for detecting signals, including but not limited to directly detecting phosphorylation of proteins using radioactive phosphorous compounds, indirectly detecting phosphorylation with antibodies specific for phosphorylated epitopes, or detecting signals from activated signal transduction proteins, such as gene expression. Preferably, gene expression is detected using a reporter gene assay. Alternatively, a downstream element of a signal transduction pathway can be modified to have reporter activity, i.e., the reporter gene can be activated by signals generated as a consequence of receptor binding, rather than as a direct result of receptor binding. Reporter genes for use in the invention encode detectable proteins, including, but are by no means limited to, chloramphenicol transferase (CAT), β-galactosidase (β-gal), luciferase, green fluorescent protein (GFP), yellow fluorescent protein (YFP), alkaline phosphatase, and other genes that can be detected, e.g., immunologically (by antibody assay).

In one embodiment, the instant invention discloses the use of the Bioluminescence Resonance Energy Transfer (BRET) method for the detection of protein-protein interactions (see, e.g., Xu et al., Proc. Natl. Acad. Sci. USA, 96:151–156, 1999; Angers et al., Proc. Natl. Acad. Sci. USA, 97:3684–3689, 2000). BRET measures the transfer of energy between a luminescent donor (e.g., luciferase expressed as a fusion protein with one of the receptors) and a fluorescent acceptor (e.g., YFP expressed as a fusion protein with one of the receptors). According to the present invention, BRET can be used (i) to examine the heterodimerization between various receptors (i.e., opioid/opioid receptors and opioid/catecholamine receptors) and (ii) to study the effect of agonist/antagonist binding on the level of dimers (see Example 4, infra).

In another embodiment, a yeast screening assay, useful for testing agonists and antagonists of mammalian G-protein coupled receptors, e.g., as disclosed in U.S. Pat. No. 5,482,832, can be used.

Specific but not limiting examples of opioid receptor-evoked cellular responses that can be monitored are summarized in Table 1.

Table 1

Opioid Receptor-Evoked Cellular Responses Direct G-protein βγ or α subunit-mediated effects activation of an inwardly rectifying potassium channel inhibition of voltage operated calcium channels (N, P, Q, and R type)

inhibition of adenylyl cyclase

Responses of unknown intermediate mechanism activation of $PLA_2$ activation of PLCβ (possibly direct G protein βγ subunit activation)

activation of MAPKinase activation of large conductance calcium-activated potassium channels activation of L type voltage operated calcium channels inhibition of T type voltage operated calcium channels direct inhibition of transmitter exocytosis Responses which are a consequence of opioid-evoked changes in other effector pathways activation of voltage-sensitive potassium channels (activation of $PLA_2$)

inhibition of M channels (activation of $PLA_2$)

inhibition of the hyperpolarisation-activiated cation channel (Ih) (Reduction in cAMP levels following inhibition of adenylyl cyclase)

elevation of intracellular free calcium levels (activation of PLCβ, activation of L type voltage operated calcium conductance)

potentiation of NMDA currents (activation of protein kinase C) inhibition of transmitter release (inhibition of adenylyl cyclase, activation of potassium channels and inhibition of voltage operated calcium channels)

decreases in neuronal excitability (activation of potassium channels) increases in neuronal firing rate (inhibition of inhibitory transmitter release-disinhibition) changes in gene expression (long-term changes in adenylyl cyclase activity, elevation of intracellular calcium levels, activation of cAMP response element binding protein (CREB)

Opioid Receptor Ligands

Various opioid receptor ligands, both synthetic molecules and endogenous opioid peptides, are known in the art (see, e.g., Tocris product literature) and are commercially available, e.g., from Tocris Cookson Inc. (USA). Tables 2 and 3 summarize some of such ligands, but are not intended to be limiting. These can serve as prototypes for drugs or drug design, based on targeting each subunit of the heterodimeric receptors of the invention. In particular, the invention contemplates designing heterodimeric receptors by linking subunit-specific ligands to each other using routine coupling chemistry.

TABLE 2

Opioid Ligands

| Receptor Type | μ-Receptor | δ-Receptor | κ-Receptor | ORL$_1$ |
|---|---|---|---|---|
| Selective agonists | endormorphin-1<br>endormorphin-2<br>DAMGO | [D-Ala$^2$]-deltorphin I<br>[D-Ala$^2$]-deltorphin II<br>DPDPE<br>DSLET<br>SNC80<br>SNC121 | enadoline<br>BRL-52537<br>ICI-199,441<br>ICI-204,448<br>N-Methyl-N-[(1S)-1-phenyl-2(1-pyrrolidinyl)-ethyl]phenylacetamide<br>(±)-1-(4-Trifluoromethyl phenyl)acetyl-2-(1-pyrro lidinyl)methylpiperidine<br>(±)-U-50488<br>(+)-U-50488<br>(−)-U-50488<br>U-54494A<br>U-69593 | nociceptin/OFQ<br>Ac-RYYRWK-NH$_2$*<br>nocstatin<br>Noc II |
| Selective antagonists | CTOP<br>Clocinnamox<br>Etonitazenyl isothiocyanate<br>β-Funaltrexamine<br>Naloxonazine | naltrindole<br>N-benzylnaltrindole<br>naltriben<br>TIPP-Ψ<br>ICI 174864<br>ICI 154129<br>BNTX | nor-binaltorphimine<br>DIPPA | None as yet** |
| Radioligands | [$^3$H]-DAMGO | [$^3$H]-deltorphin II<br>[$^3$H]-naltrindole<br>[$^3$H]-pCI-DPDPE<br>[$^3$H]-SNC 121 | [$^3$H]-enadoline<br>[$^3$H]-U69593 | $^3$[H]-nociceptin |

*Related combinatorial library hits are also selective agonists (Dooley, et al., J. Pharmacol. Exp. Ther., 283:735, 1997).
**Ac-RYYRIK-NH$_2$ has been proposed to be an ORL$_1$ antagonist (Grevel and Sadee, Science, 221:1198, 1983) whereas the putative antagonist [Phe$^1$Ψ(CH$_2$—NH)Gly$^2$]nociceptin (1–13)NH$_2$ (Guerini et al., Br. J. Pharmacol., 123:163, 1998) appears to be a partial agonist.

TABLE 3

Mammalian Endogenous Opioid Ligands

| Precursor | Endogenous Peptide |
|---|---|
| Pro-opiomelanocortin | β-Endorphin |
| Pro-enkephalin | [Met]enkephalin<br>[Leu]enkephalin<br>Metorphamide |
| Pro-dynorphin | Dynorphin A<br>Dynorphin A(1–8)<br>Dynorphin B<br>α-neoendorphin<br>β-neoendorphin |
| Pro-nociceptin/OFQ | Nociceptin |
| Not known yet* | Endomorphin-1<br>Endomorphin-2 |

In addition to the opioid receptor ligands discussed above, various other GPRC ligands particularly catecholamines, can be used to prepare bi-functional, bi-specific compounds by joining them to an opioid receptor ligand, in connection with the present invention. Examples of some ligands are described in Table 4; additional ligands can be found, inter alia, in product literature and catalogs from Tocris (http://www.tocris.com).

TABLE 4

GPRC Ligands

| Ligand | D2 | α$_2$-AR | beta2-AR |
|---|---|---|---|
| agonists | Bromocriptine mesylate<br>Dihydroergotamine mesylate<br>(−)-Quinpirole dihydrochloride | Clonidine hydrochloride<br>Gunabenz acetate<br>Guanfacine hydrochloride<br>Oxymetazoline hydrochloride<br>Rilmenidine hemifumarate<br>UK 14,304 | Clenbuterol<br>Procaterol<br>hydrochloride<br>Isopoterenol |
| antagonists | (+)-AJ 76 hydrochloride<br>Haloperidol hydrochloride<br>L-741,626<br>Pimozide<br>Remoxipride hydrochloride<br>(RS)-(±)-Sulpiride<br>(S)-(−)-Sulpiride | ARC 239 hydrochloride<br>Imiloxan hydrochloride<br>Rauwolscine hydrochloride<br>RS79948 hydrochloride<br>RS 15385 | ICI 118,551 hydrochloride |
| receptor selective compounds | AMI-193<br>3'-Fluorobenzylspiperone maleate<br>5-Hydroxy PIPAT | Agmatine sulfate | [$^3$H]-ICI 118,551 |

Bifunctional, Bispecific Compounds

As noted above, in a specific embodiment the invention provides novel compounds based on the discovery of the heterodimeric opioid receptors of the invention. While the present invention provides screens capable of identifying ligands that bind specifically to the heterodimeric receptor, the invention also contemplates modifying existing ligands, or ligands discovered in the future, by binding them together to form a bifunctional, bispecific ligand. Generally, such bifunctional bispecific ligands will be formed from a pair of individual ligands, although larger aggregates are also contemplated.

Ligands used to form bifunctional, bispecific ligands will include a reactive group for conjugation to a substituent (e.g., a free carboxylic acid group; an amino group; a sulfhydryl group; a hydroxyl group; an imidazole moiety; or an aryl group). As used herein, the term "reactive group" refers to a functional group on a ligand that reacts with a functional group on the other ligand, or on a linker or spacer used to join the ligands. The term "functional group" retains its standard meaning in organic chemistry. Preferred examples of such reactive groups for conjugation to specific substituents are carboxylic acid or sulfonic acid derivatives (including acid chlorides, anhydrides, and reactive carboxylic esters such as N-hydroxysuccinimide esters), imidoesters, diazonium salts, isocyanates, isothiocyanates, halonitrobenzenes, halocarbonyl compounds, maleimides, sulfur mustards, nitrogen mustards, and aziridines. Such groups are found, inter alia, on the endogenous peptide opioids. Various cross-linking chemistries known in the art can be used to form the bifunctional, bispecific compounds. Examples of such reagents are described below.

Functional groups reactive with primary amines.

Reactive groups that would form a covalent bond with primary amines include, but are not limited to, acid chlorides, anhydrides, reactive esters, $\alpha,\beta$-unsaturated ketones, imidoesters, and halonitrobenzenes. Various reactive esters with the capability of reacting with nucleophilic groups such as primary amines are available commercially, e.g., from Pierce (Rockford, Ill.).

Functional groups reactive with carboxylic acids.

Carboxylic acids in the presence of carbodiimides, such as EDC, can be activated, allowing for interaction with various nucleophiles including primary and secondary amines. Alkylation of carboxylic acids to form stable esters can be achieved by interaction with sulfur or nitrogen mustards or haptens containing either an alkyl or aryl aziridine moiety.

Functional groups reactive with aromatic groups.

Interaction of the aromatic moieties can be accomplished by photoactivation of an aryl diazonium compound in the presence of the aromatic moiety. Thus, modification of the aryl side chains of histidine, tryptophan, tyrosine, and phenylalanine, particularly histidine and tryptophan, can be achieved by the use of such a reactive functionality.

Functional groups reactive with sulfhydryl groups.

There are several reactive groups that can be used to modify sulfhydryl groups. Molecules containing an $\alpha,\beta$-unsaturated ketone or ester moiety, such as maleimide, provide a reactive functionality that can interact with sulfhydryl as well as amino groups. In addition, a reactive disulfide group, such as 2-pyridyl-dithio group or a 5,5'-dithio-bis-(2-nitrobenzoic acid) group, can react as well. Some examples of reagents containing reactive disulfide bonds include N-succinimidyl3-(2-pyridyldithio)-propionate (Carlsson et al., Biochem J., 173:723–737,1978), sodium S-4-succinimidyl oxycarbonyl-alpha-methylbenzylthiosulfate, and 4-succinimidyloxycarbonyl-alpha-methyl-(2-pyridyldithio)toluene. Some examples of reagents comprising reactive groups having a double bond that reacts with a thiol group include succinimidyl 4-(N-maleimidomethyl) cyclohexahe-1-carboxylate and succinimidyl m-maleimidobenzoate.

Other functional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. Many of the above-mentioned reagents and their sulfonate salts are available commercially, e.g., from Pierce (Rockford, Ill.).

Synergistic Compositions

It has also been found, as exemplified infra, that the heterodimeric opioid receptors of the invention bind synergistically to combinations of ligands (non-linked together), e.g., agonists or antagonists for each of the heterodimeric receptor subunits. Thus, the invention further provides such synergistic compositions, e.g., comprising combinations of the ligands described above with at least one member of such combination interacting with each subunit of the heterodimeric receptor.

Pharmaceutical Compositions

The compounds and compositions of the invention can be formulated as pharmaceutical compositions by admixture with a pharmaceutically acceptable carrier or excipient. Preferably, the compounds or compositions are provided in a therapeutically effective amount to an animal in need of treatment therewith, e.g., for relief of pain, hypertension, or some other condition. The animal subject is preferably a human, but the compounds and compositions of the invention have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

The phrase "pharmaceutically acceptable" refers to molecular entities and compositions that are physiologically tolerable and do not typically produce an allergic or similar untoward reaction, such as gastric upset, dizziness and the like, when administered to a subject. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the host. Alternatively, a therapeutically effective amount is sufficient to cause an improvement in a clinically significant condition in the host. These parameters will depend on the severity of the condition being treated, other actions, such as diet modification, that are implemented, the weight, age, and sex of the subject, and other criteria, which can be readily determined according to standard good medical practice by those of skill in the art According to the invention, the component or components of a pharmaceutical composition of the invention may be introduced parenterally, transmucosally, e.g., orally, nasally, or rectally, or transdermally. Parenteral administration includes, but is not limited to, intravenous, intra-arteriole, intramuscular, intradermal, subcutaneous, intraperitoneal, intraventricular, and intracranial administration.

In a specific embodiment, the therapeutic compound can be delivered in a vesicle, in particular a liposome (see Langer, Science, 249:1527–1533, 1990; Treat et al., in *Liposomes in the Therapy of Infectious Disease and Cancer*, Lopez-Berestein and Fidler eds., Liss: New York, pp. 353–365, 1989; Lopez-Berestein, ibid., pp. 317–327; see generally ibid.). To reduce its systemic side effects, this may be a preferred method for introducing the compound.

In yet another embodiment, the therapeutic compound can be delivered in a controlled or sustained release system. For example, a compound or composition may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng., 14:201, 1987; Buchwald et al., Surgery, 88:507, 1980; Saudek et al., N. Engl. J. Med., 321:574, 1989). In another embodiment, polymeric materials can be used (see *Medical Applications of Controlled Release*, Langer and Wise eds., CRC Press: Boca Raton, Fla., 1974; *Controlled Drug Bioavailability, Drug Product Design and Performance*, Smolen and Ball eds., Wiley, N.Y., 1984; Ranger and Peppas, J. Macromol. Sci. Rev. Macromol. Chem., 23:61, 1983; Levy et al., Science 228:190, 1985; During et al., Ann. Neurol., 25:351, 1989; Howard et al., J.Neurosurg. 71:105, 1989). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, Vol. 2, pp. 115–138, 1984). Other controlled release systems are discussed in the review by Langer (supra).

EXAMPLES

The present invention will be better understood by reference to the following Examples, which are provided by way of exemplification and not by way of limitation.

Example 1

Determination If Opioid Receptor Heterodimerization Modulates Receptor Function

This example provides biochemical and pharmacological evidence for the heterodimerization of two fully functional opioid receptors (kappa and delta), as well as evidence for covalent homodimerization of kappa receptor. This results in a new receptor that exhibits ligand binding and functional properties that are distinct from those of either receptor. Furthermore, the kappa-delta heterodimer synergistically binds highly selective agonists and potentiates signal transduction. Thus heterodimerization of these GPCRs represents a novel mechanism that modulates their function.

Materials and Methods

Abbreviations:

DTT, dithiothreitol; β-ME, 2-mercaptoethanol; IAM, iodoacetamide; NEM, n-ethylmaleimide.

Generation of Cell Lines Expressing Opioid Receptors.

Cells stably expressing epitope-tagged rat kappa or mouse delta receptors were generated as described previously (Cvejic et al., J. Biol. Chem., 271:4073–4076, 1996). HEK293 or COS cells co-expressing myc-tagged kappa, with FLAG-tagged-kappa, delta, or mu receptors were generated by transfecting cells using calcium phosphate precipitation (Cvejic and Devi, supra). Cells were collected after 72 hours of transient expression For stable expression, CHO cells were transfected with the FLAG-tagged kappa receptor cDNA in a geneticin selectable vector and myc-tagged delta receptor cDNA in a hygromycin selectable vector (pCEN4, Invitrogen) and were selected with 500 μg/ml each of Geneticin (G418) and Hygromycin (GIBCO). Surface expression was confirmed by flow cytometry using monoclonal anti-FLAG ('M1', Sigma) and polyclonal anti-myc (c-Myc A14, Santa Cruz) antibodies. Three individual clones expressing kappa plus delta receptors at a ratio of approximately 1:1 were used for further studies.

Detection of Dimerization by Immunoprecipitation Techniques and Western Blotting.

Cross-linking with DSP (dithiobis-succinimydyl propionate, Pierce), SDS-PAGE and Western blotting were carried out with lysates of whole cells or membranes essentially as described (Cvejic and Devi, supra) except that cells were lysed in buffers containing the protease inhibitor cocktail (10 μg/ml leupeptin, 10 μg/ml aprotinin, 10 mM EDTA, 1 mM EGTA, 10 μg/ml Bacitracin, 1 mM pepstatin A, 0.5 mM PMSF and 1 mM E-64) and 100 mM iodoacetamide at 4° C. for 60 minutes (or at 23° C. when lysing with SDS buffer). In the majority of experiments Tx/G buffer (300 mM NaCl, 1% Triton X-100, 10% glycerol, 1.5 mM $MgCl_2$, and 1 mM $CaCl_2$ in 50 mM Tris-Cl, pH 7.4) was used for solubilization. Other solubilization buffers were, RIPA (1% NP-40, 0.5% Deoxycholate, 0.5% SDS, 300 mM NaCl), CHAPS (0.5% in 50 mM $NaPO_4$ buffer, pH 7.4), DM (0.5% Dodecyl β-Maltoside in 50 mM Tris-Cl, pH 7.4) and SDS (2% SDS in 50 mM Tris-Cl, pH 6.8). For immunoprecipitation, 100–200 μg of proteins were incubated overnight at 4° C. with 5–10 μg of polyclonal anti-myc antibody. Imunocomplexes were isolated by incubation with 10% v/v of protein A-Sepharose and analyzed by western blotting using monoclonal anti-FLAG antibody as described (Cvejic and Devi, supra). Kappa receptors are differentially glycosylated in CHO and COS cells; this could account for differences in the size of monomers and dimers. 10 mM DTT was added to the immunoprecipitate to create weak reducing conditions and eliminate cross-reactivity with nonspecific proteins. A portion of dimers were converted to monomers under these conditions.

Binding Assays.

For membrane preparation, HEK293 cells expressing single or combinations of receptors were washed with PBS, collected with a rubber policeman in 5 mM Tris-Cl buffer, pH 7.4 and incubated for 30 min at room temperature. Cells were disrupted by sonication and subjected to low speed centrifugation to remove organelles and nuclei. The resulting supernatant was subjected to centrifugation at 50,000×g for 10 min, membranes collected, washed 3 times, resuspended in 50 mM Tris-Cl, pH 7.4 containing a protease inhibitor cocktail and stored at −80° C. Membranes were homogenized upon thawing and approximately 30–50 μg of membrane proteins were incubated with 0.5 nM or 5 nM $^3$H-diprenorphine (40 Ci/mmol, NEN/Dupont) for 60 min at 37° C. in the absence or presence of 5–8-fold excess of unlabeled ligands; 1 μM unlabeled diprenorphine was used to obtain specific binding. 5 nM $^3$H-diprenorphine labels all receptors in kappa-delta expressing cells. Approximately 45% of the specific binding is not displaced by either 10 μM DPDPE or 10 μM U-69593; this can be selectively labeled by 0.5 nM $^3$H-diprenorphine, so all studies characterizing kappa-delta heterodimer were carried out with 0.5 nM $^3$H-diprenorphine. IC50 values were determined from displacement curves using GraphPad Prism 2.0 and the inhibition constant (Ki) values were determined using the Cheng-Prusoff equation (Cheng and Prusoff, Biochem. Pharmacol., 22:3099–3102, 1973).

Internalization Assays.

Ligand-induced internalization was carried out by flow cytometry as described previously (Trapaidze et al., J. Biol. Chem., 271:29279–29285, 1996) except that FITC-conjugated anti-mouse antibody was used to detect the monoclonal anti-FLAG antibody ('M1', Sigma) bound to FLAG-kappa receptors and Phycoerythrin-conjugated anti-rabbit antibody to detect the polyclonal anti-myc antibody (c-Myc A14, Santa Cruz) bound to myc-tagged delta receptors.

Functional Assays.

Figure 3A:
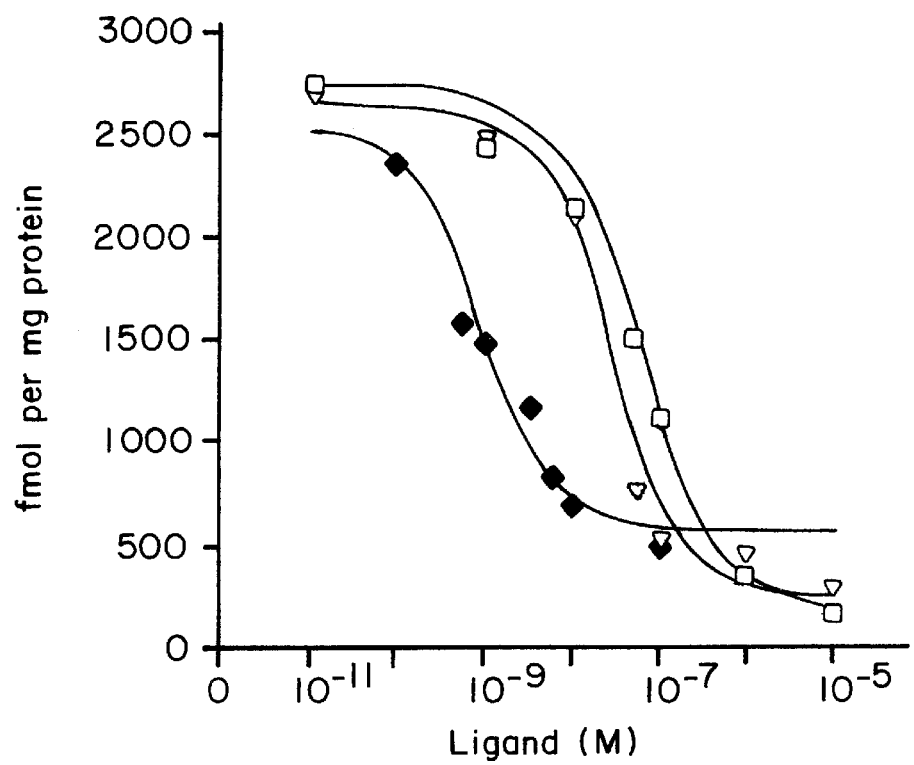
FIGS. 3A, B, C, D, E, and F. Ligand binding and functional properties. Competition of $^3$H-diprenorphine binding by U-69593 (square), nor-BNI (triangle), diprenorphine (star), DPDPE (circle) and TIPPY (diamond) in membranes from cells expressing kappa (A) delta (B) or kappa and delta (C) receptors. Displacement of $^3$H-diprenorphine by U-69593 in the presence of 10 μM DPDPE (triangle) or DPDPE in the presence of 10 μM U-69593 (diamond) (D). Decrease in intracellular cAMP (E) or increase in phospho-MAP kinase (F) by U-69593 (square), DPDPE (circle) or U-69593+DPDPE (triangle). Activation of homodimers in these cells could account for the effect seen with individual agonists. Error bars represent SEM (n=3–4).
Figure 3B:
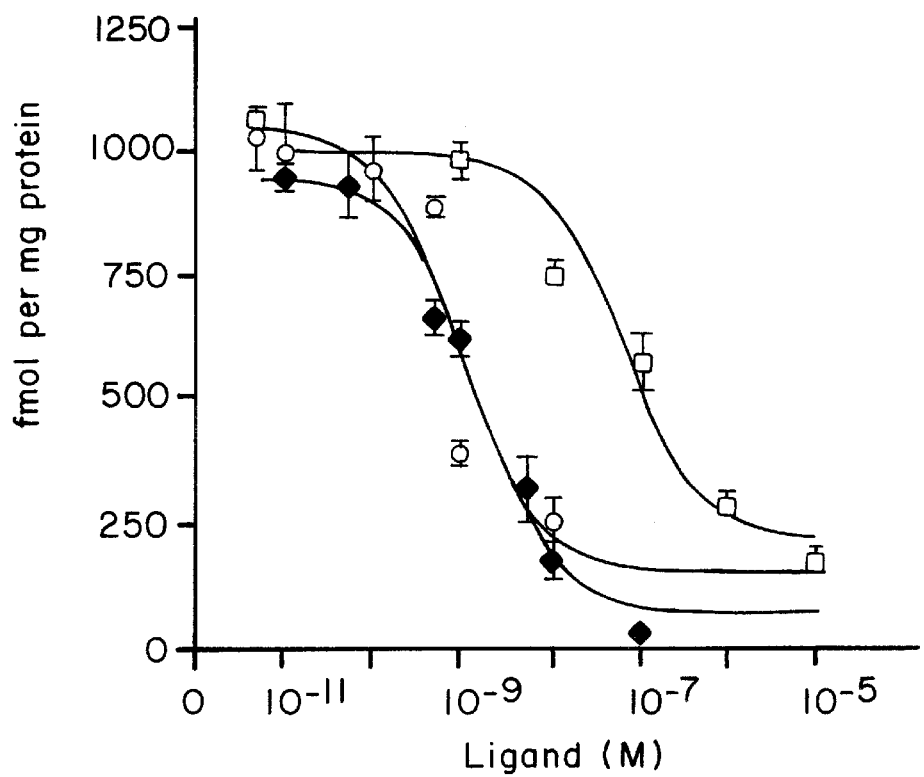
Figure 3C:
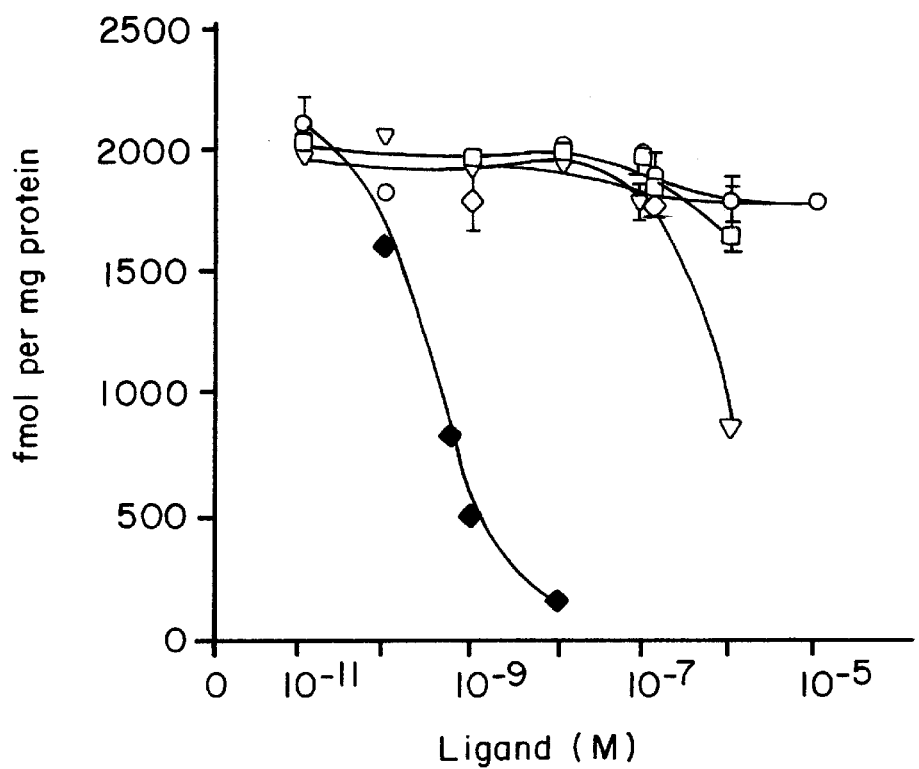
Figure 3D:
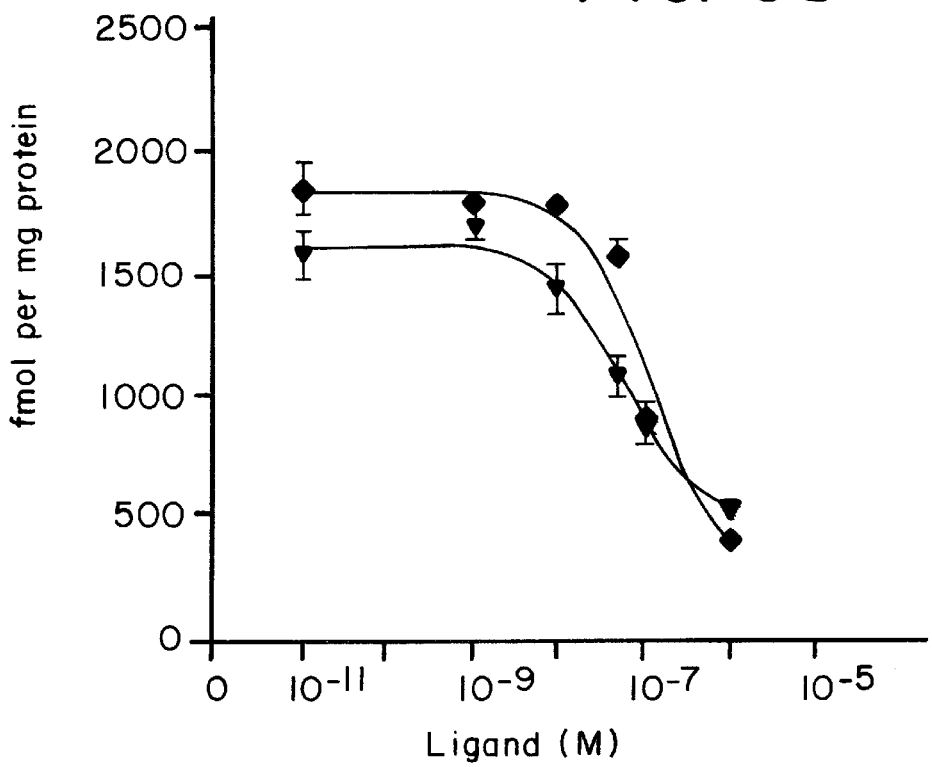
Figure 3E:
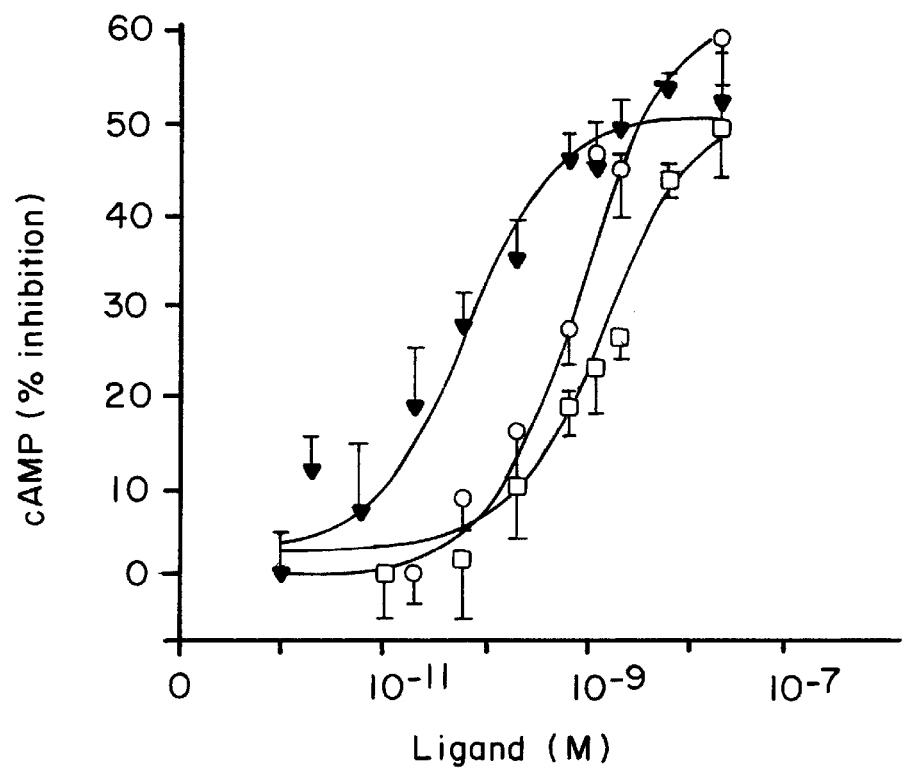
Figure 3F:
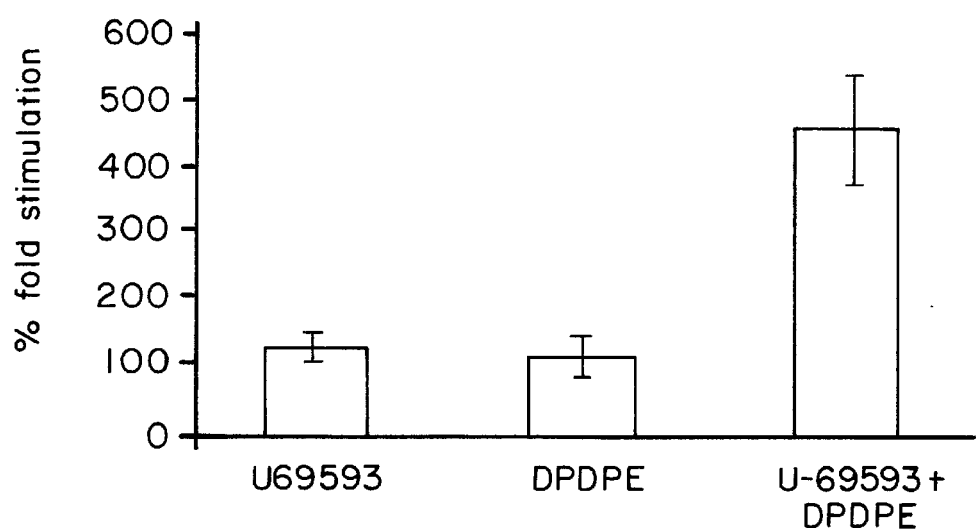

CHO cells co-expressing approximately 1:1 ratio of kappa and delta receptors were treated with various doses of agonists (2×DPDPE, 2×U-69593 or 1×DPDPE+1×U-69593) for 5 min at 37° C. The intracellular cAMP level was measured by a radioimmunoassay as described previously (Cvejic et al., supra). The level of phosphorylated MAPK was determined by Western blotting (Polakiewicz et al., J. Biol. Chem., 273:12402–12406, 1998). Protein loading in the blots was standardized using anti-tubulin antibody (Sigma) to detect tubulin. NIH Image 1.61 software was used to densitize and quantify phospho-MAPK levels. The extent of MAPK phosphorylation in cells treated with 2 nM DPDPE or 2 nM U-69593 or 1 nM DPDPE+1 nM U-69593 is shown in FIG. 3F (upper panel). % fold-stimulation refers to the agonist-induced increase in phospho-MAPK levels over untreated levels (taken as control, 100%).

Results

Determination Of The Molecular Structure Of Opioid Receptors.

Figure 1B:
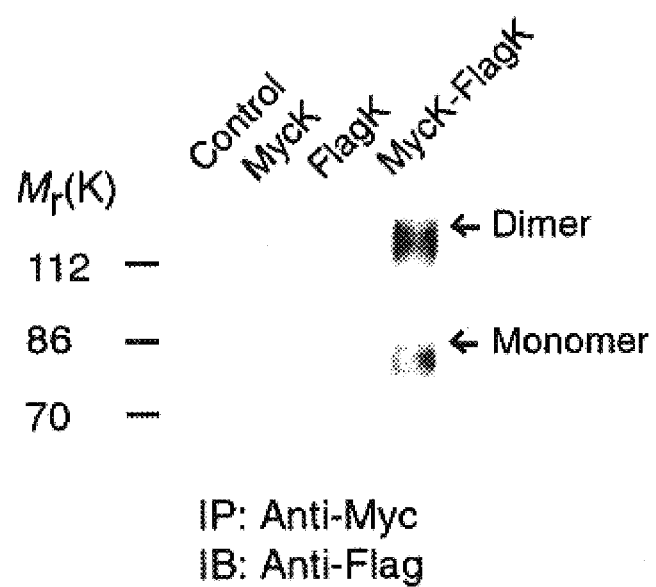
Figure 1C:
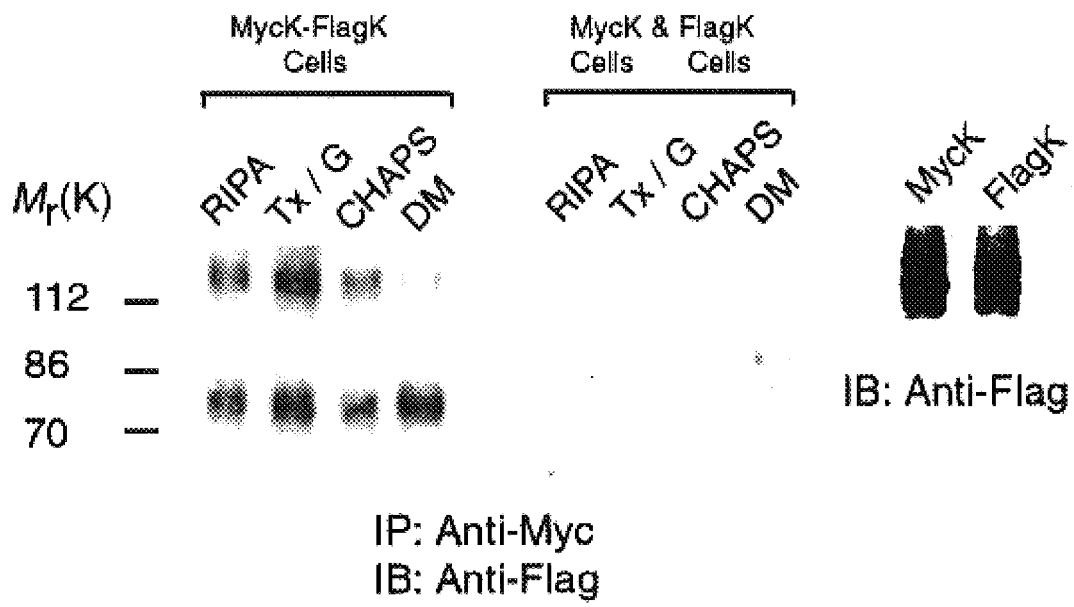
Figure 1D:
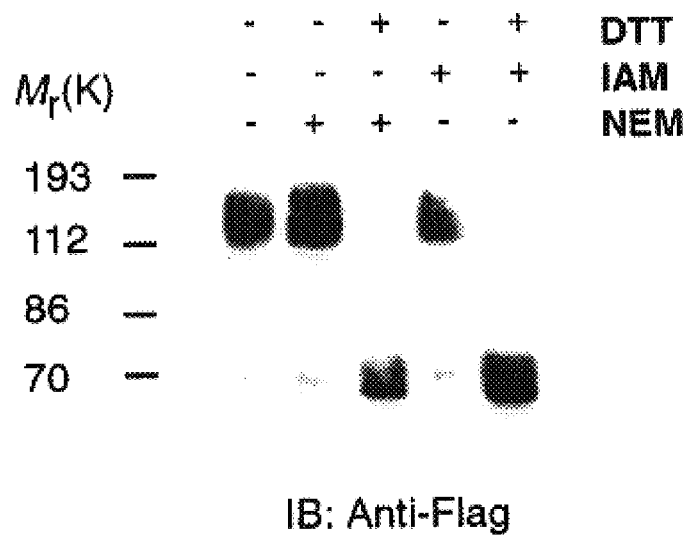
Figure 1E:
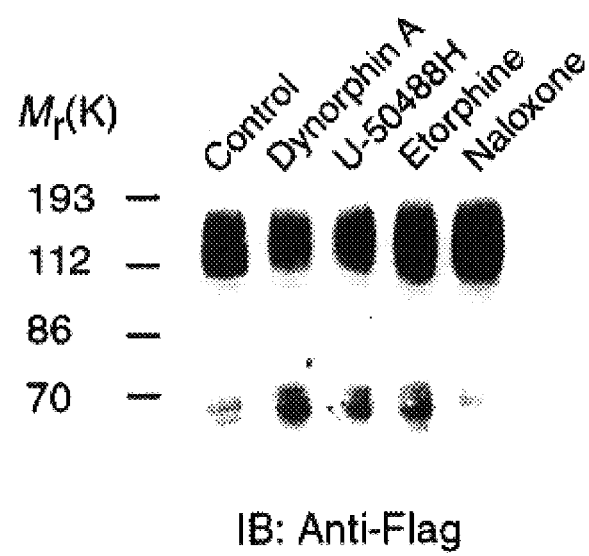

The majority of kappa receptors exist as 130 kDa dimers both in the presence and in the absence of a cross-linker (FIG. 1A). The dimers are stable in 10% SDS (not shown). This is unexpected since delta receptors exhibit little or no dimeric forms in the absence of the crosslinker; i.e., crosslinking is required to stabilize delta receptor dimers (FIG. 1A). The identity of the kappa-containing dimer was confirmed by immunoprecipitation experiments using differentially tagged receptors. An antibody to the myc-tagged receptor is able to co-precipitate FLAG-tagged receptors from cells expressing both myc-tagged and FLAG-tagged receptors (FIG. 1B). The homodimerization of kappa receptors is not induced by detergents or extraction conditions since receptors could be co-precipitated under a variety of conditions and only from cells co-expressing myc- and FLAG-tagged receptors (FIG. 1C) and not from a mixture of cells individually expressing the receptors (FIG. 1C). Kappa dimers are destabilized in the presence of reducing agents (FIG. 1D) suggesting the involvement of disulfide bonds in receptor dimerization. Recently, both the metabotropic glutamate receptor 5 and the calcium sensing receptor were shown to dimerize via disulfide bonds (Romano et al., J. Biol. Chem., 271:28612–28616, 1996; Bai et al., J. Biol. Chem., 273:23605–23610, 1998). Agonist treatment does not induce monomerization of kappa receptor dimers (FIG. 1E); this is in contrast to delta receptor dimers which monomerize in the presence of agonists (Cvejic and Devi, supra). These results indicate that the properties of kappa receptor dimers are different from those of delta receptor dimers.

Heterodimeric Properties of Kappa Receptors.

Figure 2A:
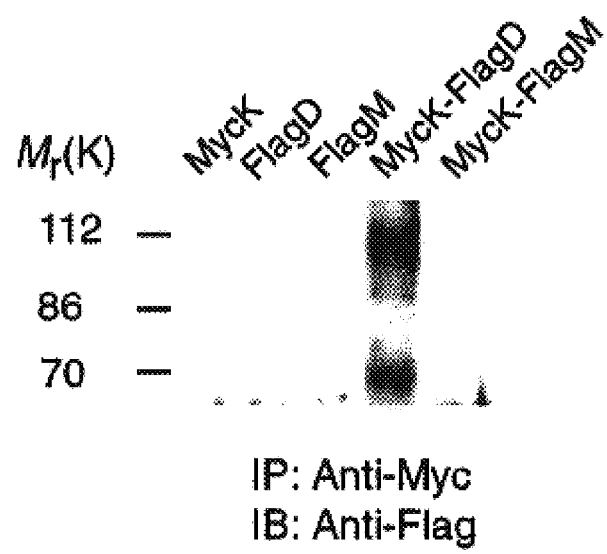
FIGS. 2A, B, C, and D. Characterization of kappa-delta heterodimers. Kappa-delta heterodimers can be immunoprecipitated only from myc-kappa and FLAG-delta expressing cells and not from myc-kappa and FLAG-mu expressing cells (A). Kappa-delta heterodimers can be immunoprecipitated under a variety of extraction conditions and not from mixture of cells individually expressing these receptors (B). Expression of myc- or FLAG-tagged receptors in each cell line was confirmed by immunoblotting (right panel). Treatment with 5% β-ME for 5 min results in the destabilization of dimers (C). Internalization of receptors in response to 1 μM etorphine for 60 minutes (O). Significant differences from untreated controls are indicated, *p<0.05; ***p<0.005 (n=3).
Figure 2B:
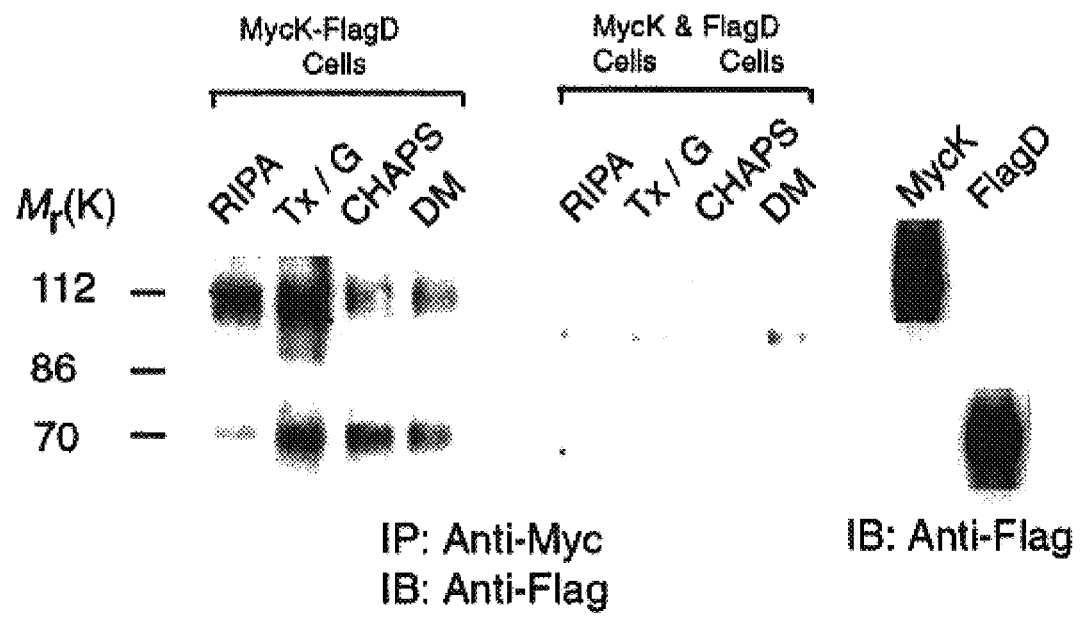
Figure 2C:
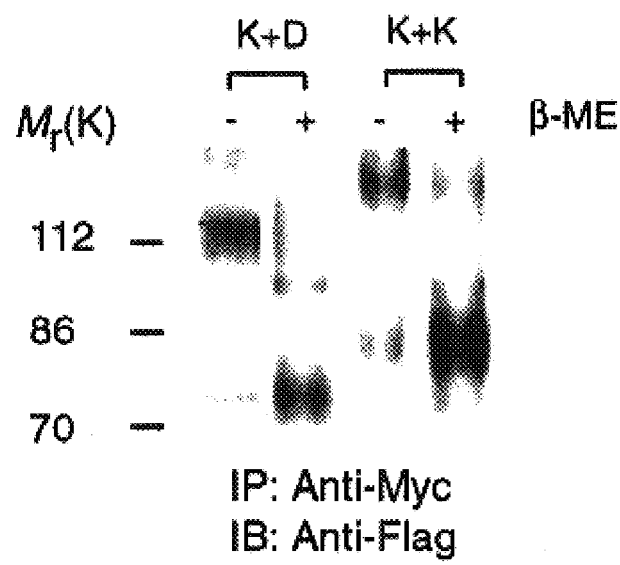

The ability of kappa receptors to heterodimerize with delta or mu receptors was investigated by co-expressing myc-tagged kappa receptors either with FLAG-tagged delta receptors or FLAG-tagged mu receptors. FLAG-tagged delta receptors were detected in material immunoprecipitated using antibodies specific for myc-tagged kappa receptors (FIG. 2A). In contrast, FLAG-tagged mu receptor could not be detected under similar co-precipitation conditions (FIG. 2A). These results indicate that kappa receptors selectively dimerize with delta but not mu opioid receptors. Kappa-delta heterodimers are stable in a variety of detergents and are not induced during solubilization/immunoprecipitation procedures (FIG. 2B). Also, kappa-delta heterodimers are destabilized by a reducing agent (FIG. 2C) indicating that disulfide bonds are involved in kappa-delta heterodimerization.

Effect of Heterodimerization On Receptor Trafficking.

Figure 2D:
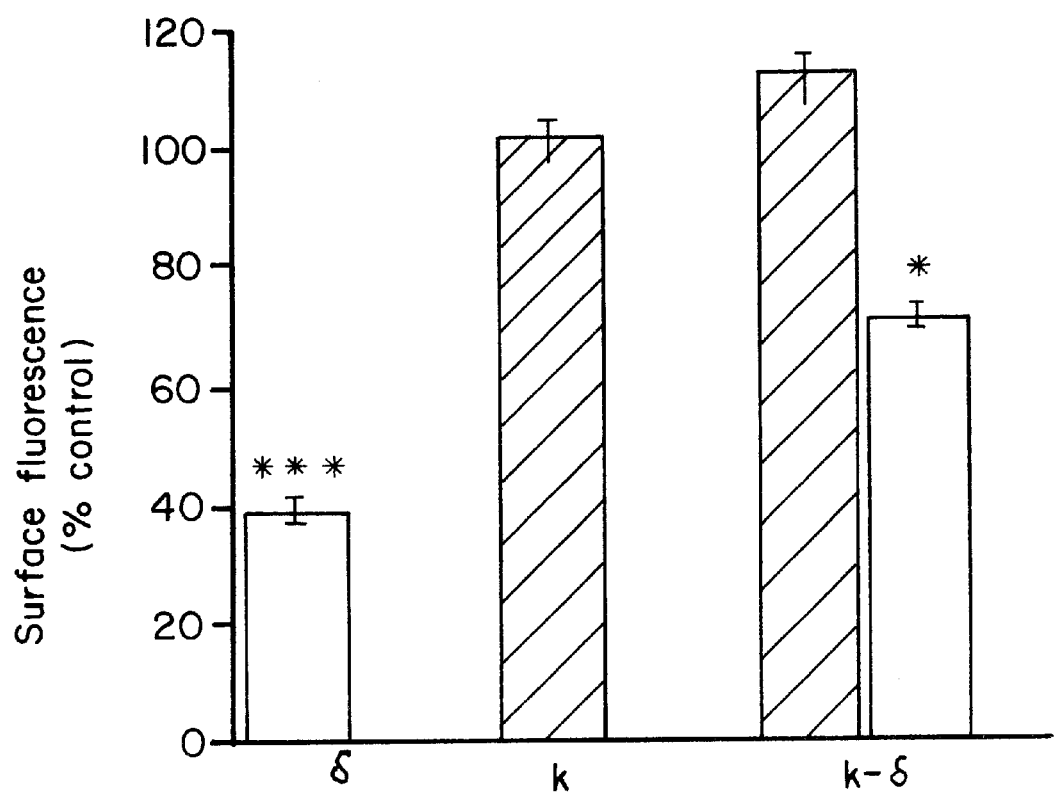

The effect of heterodimerization on receptor trafficking was determined using cells co-expressing kappa and delta receptors treated with etorphine. Etorphine is a potent non-selective opioid agonist that binds both delta and kappa receptors with high affinity. As was shown previously (Trapaidze, supra; Keith et al., J. Biol. Chem., 271:19021–19024, 1996; Chu et al., J. Biol. Chem., 272:27124–27130, 1997) etorphine is able to induce robust internalization of delta receptors but not kappa receptors in cells individually expressing these receptors (FIG. 2D). In contrast, etorphine is not able to induce significant internalization of either receptor in cells expressing both kappa and delta receptors; the internalization of delta homodimers in these cells could account for the observed approximate 25–30% reduction in surface fluorescence (FIG. 2D). These results indicate that heterodimerization alters the trafficking properties of these receptors.

Comparison Of Ligand Binding Properties Of Opioid Receptor Heterodimers.

The ligand binding properties of kappa-delta heterodimers were compared to the properties of kappa or delta receptors as shown on Table 5.

TABLE 5

Ligand Binding Properties of Kappa-Delta Heterodimer

| Ligand | Kappa (Ki | Delta (Ki nM) | Kappa-Delta (Ki |
|---|---|---|---|
| Agonists | | | |
| U-69593 | 14.4 ± 0.2 | >1000 | >1000 |
| DPDPE | >1000 | 21.8 ± 2.1 | >1000 |
| Dynorphin A | 1.3 ± 0.41 | 56.8 ± 0.3 | 5.6 ± 0.3 |
| EKC | 5.7 ± 0.79 | 105 ± 1.2 | 2.6 ± 0.2 |
| Etorphine | 1.5 ± 0.73 | 7.9 ± 0.03 | 7.0 ± 0.3 |
| Bremazocine | 0.4 ± 0.11 | 7.5 ± 0.03 | 1.2 ± 0.1 |
| Antagonists | | | |
| nor-BNI | 4.9 ± 0.3 | 31.8 ± 1.2 | 126 ± 9.6 |
| TIPP Ψ | >1000 | 0.28 ± 0.6 | >1000 |
| BNTX | 172 ± 19 | 5.2 ± 0.6 | 98 ± 19 |
| Naltrinole | 44.3 ± 1.1 | 1.0 ± 0.21 | 44 ± 1.1 |
| Naloxone | 14.9 ± 3.4 | 43.4 ± 0.3 | 7.5 ± 0.4 |
| Diprenorphine | 0.71 ± 0.27 | 1.43 ± 1.1 | 0.3 ± 0.1 |
| Combination of Ligands | | | |
| U-69593 (+10 μM DPDPE) | 14.4 ± 0.4 | — | 9.2 ± 1.4 |
| DPDPE (+10 μM U-69593) | — | 24.8 ± 1.6 | 20.0 ± 1.3 |
| nor-BNI (+10 μM TIPP Ψ) | — | — | 0.02 ± 0.003 |
| U-69593 (+10 μM TIPP Ψ) | — | — | >1000 |

Ligand affinities were determined by competition assays using $^3$H-diprenorphine as described. Mean ± SEM (n = 3–4). nor-BNI, nor-binaltorphimine; BNTX, 7-Benzylidenenaltrexone; EKC, ethylketocyclazocine; DPDPE, [D-Pen2, D-Pen5]enkephalin; - not done.

The ability of highly selective agonists (Lahti et al., Eur. J. Pharmacol., 109:281–284, 1985; Roth et al., J. Med.

Chem., 258:299–303, 1990) and antagonists (Portoghese et al., Life Sci., 40:1287–1292, 1987; Schiller et al., J. Med. Chem., 36:3182–3187, 1993) to compete with $^3$H-diprenorphine (a non-selective opioid antagonist) in membranes from cells expressing either kappa, delta or both kappa and delta receptors was determined (FIGS. 3A–C). Kappa receptors exhibit high affinities for the kappa-selective agonist (U-69593) and antagonist (nor-BNI). Similarly, delta receptors exhibit high affinities for the delta-selective agonist (DPDPE) and antagonist (TIPPΨ). In contrast, kappa-delta heterodimers do not exhibit significant affinity for either kappa- or delta-selective agonists or antagonists (FIG. 3C; Table 5). However, the heterodimer exhibits high affinity for partially selective ligands (Table 5). The properties of these heterodimers are virtually identical to the properties of the previously reported kappa-2 receptor subtype (Zukin et al., Proc. Natl. Acad. Sci. USA, 85:4061–4065, 1988). Several pharmacological studies have reported the presence of additional subtypes of kappa opioid receptors (Nock, in *The Pharmacology of Opioid Peptides*, L. Tseng ed., pp.29–56, Harwood Acad. Publishers, 1995) as well as delta (Traynor and Elliott, Trends in Pharm. Sci., 14:84–86, 1993; Zaki et al., Ann. Rev. Pharmacol. Toxicol., 36:379–401, 1996). However, cDNAs corresponding to these subtypes have not yet been identified despite large-scale efforts by a number of laboratories. Recent work with delta receptor knockout mice shows that both delta1 and delta2 receptor subtypes are eliminated in these animals, suggesting that the delta receptor locus encodes both these subtypes (Mathes et al., J. Neurosci., 18:7285–95, 1998). It is possible that heterodimerization of delta or kappa receptors with other GPCRs could form a molecular basis for other receptor subtypes.

It was then determined if the kappa-delta heterodimer could synergistically bind selective agonists. In the presence of the delta-selective agonist (DPDPE), the kappa agonist (U-9593) was able to bind the heterodimer with high affinity (FIG. 3D, Table 5). Similarly, in the presence of kappa-selective agonist (U-69593), the delta agonist (DPDPE) is able to bind with high affinity (FIG. 3D, Table 5). Interestingly, while a combination of two selective antagonists is also able to bind with high affinity, a combination of a selective agonist (U-69593) with a selective antagonist (TIPPΨ) is not (Table 5). Also, synergistic binding is not observed in membranes from cells individually expressing kappa or delta receptors (not shown). Taken together, these results imply that kappa-delta heterodimerization results in a new binding site which is able to synergistically bind highly selective ligands.

To determine if the synergistic binding of agonists leads to potentiation of effector function, the previous observation that the activation of opioid receptors by agonists causes a decrease in the level of intracellular cAMP as well as an increase in the level of phosphorylated MAPK was used (Jordan and Devi, Br. J. Anaesthesia, 81:12–19, 1998). The potency of individual agonists to reduce intracellular cAMP levels was found to be about 10–20-fold lower than the combination of both agonists to reduce cAMP levels (FIG. 3E). Similarly, there was a significant potentiation of MAPK phosphorylation by simultaneous treatment of cells with both agonists as compared to individual agonists (FIG. 3F). These results strongly suggest that the kappa-delta heterodimer represents a functional receptor which exhibits a synergistic activation by selective ligands.

Discussion

These data provide biochemical and functional evidence for opioid receptor heterodimerization. This is the first direct evidence of the heterodimerization of opioid receptor types and of two fully functional GPCRs. The heterodimers exhibit greatly reduced affinities for their selective ligands. Interestingly, selective agonists can co-operatively bind to heterodimers and induce synergistic functional responses. Heterodimerization could be a mechanism for the activation of receptors upon the co-release of selective endogenous peptides. Alternatively, kappa-delta heterodimers could represent a hitherto uncharacterized receptor for a specific endogenous opioid peptide. The number of endogenous opioid peptides are far greater than the number of cloned opioid receptors (Lord, supra). Opioid receptor subtypes resulting from heterodimerization of opioid receptors with other GPCRs could be targets for the action of these endogenous peptides. The physical interactions between GPCRs has enormous ramifications in understanding the complexity of regulation of their function. Heterodimerization of opioid receptors also points to additional targets for the development of drug therapies.

Example 2

Heterodimerization of Mu and Delta Opioid Receptors. A Novel Super High Affinity Morphine Binding Site Uncovered by Opiate Synergy Materials and Methods Generation of Cell Lines Expressing Opioid Receptors and Isolation of Receptor Heterodimers by Immunoprecipitation.

Cells expressing mu-delta receptors were generated by transfecting HEK-293 cells or CHO cells with FLAG-tagged mouse mu receptor cDNA and myc-tagged delta receptor cDNA using standard calcium phosphate precipitation. In the majority of the studies, the mu:delta receptor ratio for HEK cells was approximately 1:3 and for CHO cells was 3:1. HEK-293 cells transiently transfected with tagged opioid receptor were lysed in buffer Tx/G (300 mM NaCl, 1% Triton X-100, 10% glycerol, 1.5 mM $MgCl_2$, and 1 mM $CaCl_2$ in 50 mM Tris-Cl, pH 7.4), containing a protease inhibitor cocktail and 10–100 mM iodoacetamide for 1 h at 4° C. The protease inhibitor cocktail contained 10 μg/ml leupeptin, 10 μg/ml aprotinin, 10 mM EDTA, 1 mM EGTA, 10 μg/ml Bacitracin, 1 mM pepstatin A, 0.5 mM PMSF and 1 mM E-64. Approximately 10 μg of protein was resolved on a nonreducing 8% SDS-PAGE and subjected to Western blotting as described (Cvejic et al., supra). For immunoprecipitation, 100–200 μg of protein was incubated with 1–2 μg of polyclonal anti-myc antibody overnight at 4° C. Imunocomplexes were isolated by incubation with 10% v/v Protein A-Sepharose (Sigma) for 2–3 hours. The beads were washed 3× with the buffer G and analyzed by western blotting using monoclonal anti-FLAG antibody as described (Cvejic et al., supra).

Membrane Binding Assays.

The HEK or CHO cells were disrupted by sonication. The cell membranes were collected as described (Jordan and Devi, Nature, 399:697–700, 1999). For most assays, membranes (representing 5–10 μg of total protein that would give 5–10% specific $^3$H-diprenorphine binding) were incubated with 2 nM [$^3$H]-diprenorphine in 50 mM Tris-Cl pH 7.4 buffer for 60 minutes at 37° C. in the absence or presence of indicated concentrations of unlabeled ligands in a final volume of 500 μl. 1 μM unlabeled diprenorphine was used to obtain the background. The membranes were then collected on Whatman GF-B filters, washed with cold 50 mM Tris-Cl pH 7.4, and then incubated in scintillation liquid for 16 h. IC50 values were determined from displacement curves using GraphPad Prism 2.0 and the inhibition constant (Ki) using the Cheng-Prusoff equation (Cheng and Prusoff, supra).

Whole Cell Binding assays.

SK-N-SH cells that endogenously express mu and delta receptors, or CHO cells expressing FLAG-tagged mu alone or co-expressing FLAG-tagged mu and myc-tagged delta receptors were plated on 24-well plates, and after 18 h the media was removed and cells were incubated with $^3$H-DAMGO (3 nM final concentration) in 50 mM Tris-HCl buffer pH 7.4 (Buffer A) in a final volume of 300 μl. The binding was carried out for 2 hours at 37° C. in the absence or presence of varying concentrations of TIPPΨ, Deltorphin II, DPDEP, naltriben or BNTX. At the end of the incubation plates were transferred to 4° C. and the wells were washed 5 times with 0.5 ml of cold 50 mM Tris-HCl, pH 7.4. Cells were dissolved in 100 μl 1N NaOH, collected, neutralized with 100 μl 1N HCl and the radioactivity was measured in Biosafe scintillation fluid. Non-specific binding was determined in the presence of 100 nM DAMGO or diprenorphine. Concentrations of $^3$H-DPDPE from 0.1 to 20 nM were used for saturation analysis.

Results

Figure 4:
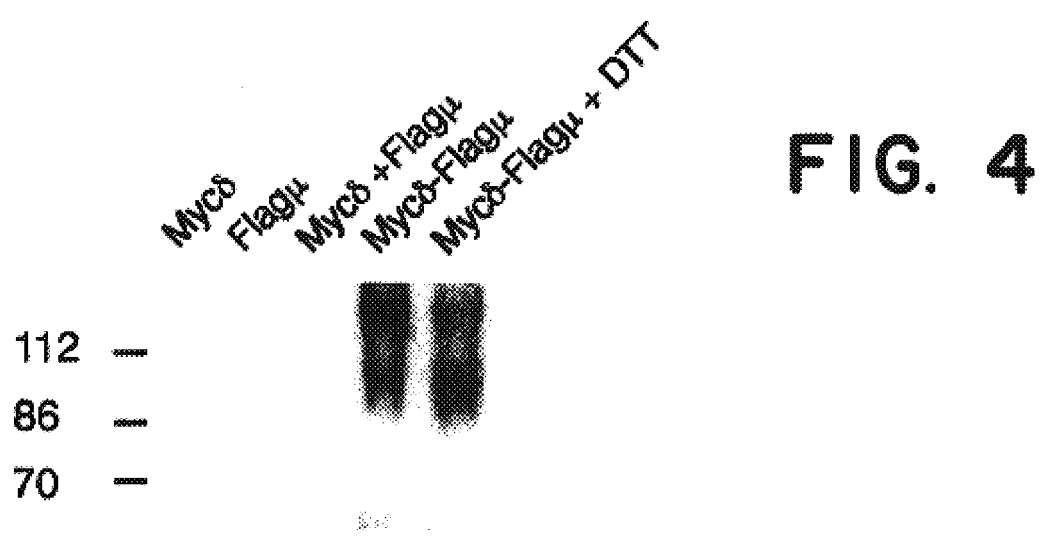
FIG. 4. Mu and delta receptors interact with each other to form heterodimers. Immunoprecipitation of cell lysates from HEK-293 cells individually expressing either FLAG-mu or myc-delta receptors, mixed cells individually expressing FLAG-mu or myc-delta receptors, or cells co-expressing FLAG-mu and myc-delta was carried out using anti-myc antibodies. Western blotting of these immunocomplexes using anti-FLAG antibodies shows an approximately 150 kDa protein representing mu-delta heterodimers only in cells co-expressing both FLAG-mu and myc-delta receptors. Pre-treatment of cells with 1 mM DTT results in the destabilization of dimers.

The ability of mu receptors to dimerize was predicted by studies showing that the dimeric analogs of morphine exhibited higher affinity and several-fold greater potency than their monomeric forms (Cvejic et al., supra). This was directly tested by co-expressing FLAG-tagged mu receptors with myc-tagged delta receptors. Cell lysates were immunoprecipitated with polyclonal anti-myc antibodies and western blotted with monoclonal anti-FLAG antibody (Cvejic et al., supra). Under these conditions mu receptors were found to associate with delta receptors to form an approximately 150 kDa heterodimer (FIG. 4). These heterodimers are not induced during solubilization/immunoprecipitation conditions since lysates of a mixture of cells individually expressing either mu or delta did not show the presence of a heterodimer (FIG. 4). These mu-delta heterodimers are stable in a variety of detergents and extraction conditions (not shown). Like kappa-delta heterodimers, the mu-delta heterodimers were also sensitive to reducing agents since treatment of cells with 1 mM DTT for 30 min followed by 5 mM iodoacetamide resulted in the destabilization of dimers (FIG. 4, lane 5).

Figure 5:
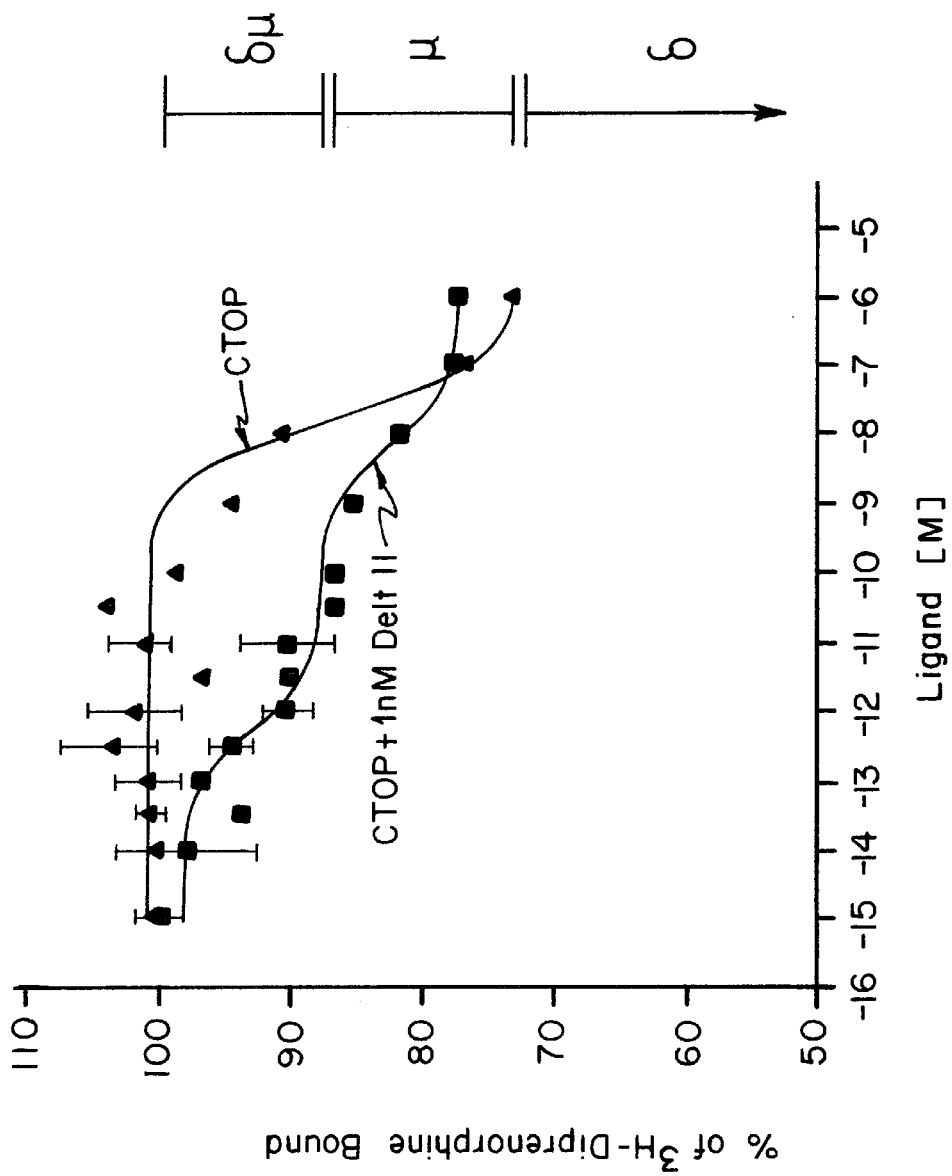
FIG. 5. Ligand binding properties in membranes of HEK-cells expressing mu-delta heterodimers were evaluated by measuring the displacement of $^3$H-diprenorphine binding by CTOP in cells expressing mu-delta heterodimers. Membranes were incubated with $^3$H-diprenorphine in the absence or in the presence of various doses of CTOP alone or CTOP in the presence of 1 nM TIPPΨ as described above. We find a single binding site for CTOP in the absence of TIPPΨ and a second super high affinity binding site in the presence of 1 nM TIPPΨ. Data from a representative of experiment (out of 3–7) is shown; error bars represent SEM; variation between experimernts was less than 10%.
Figure 6A:
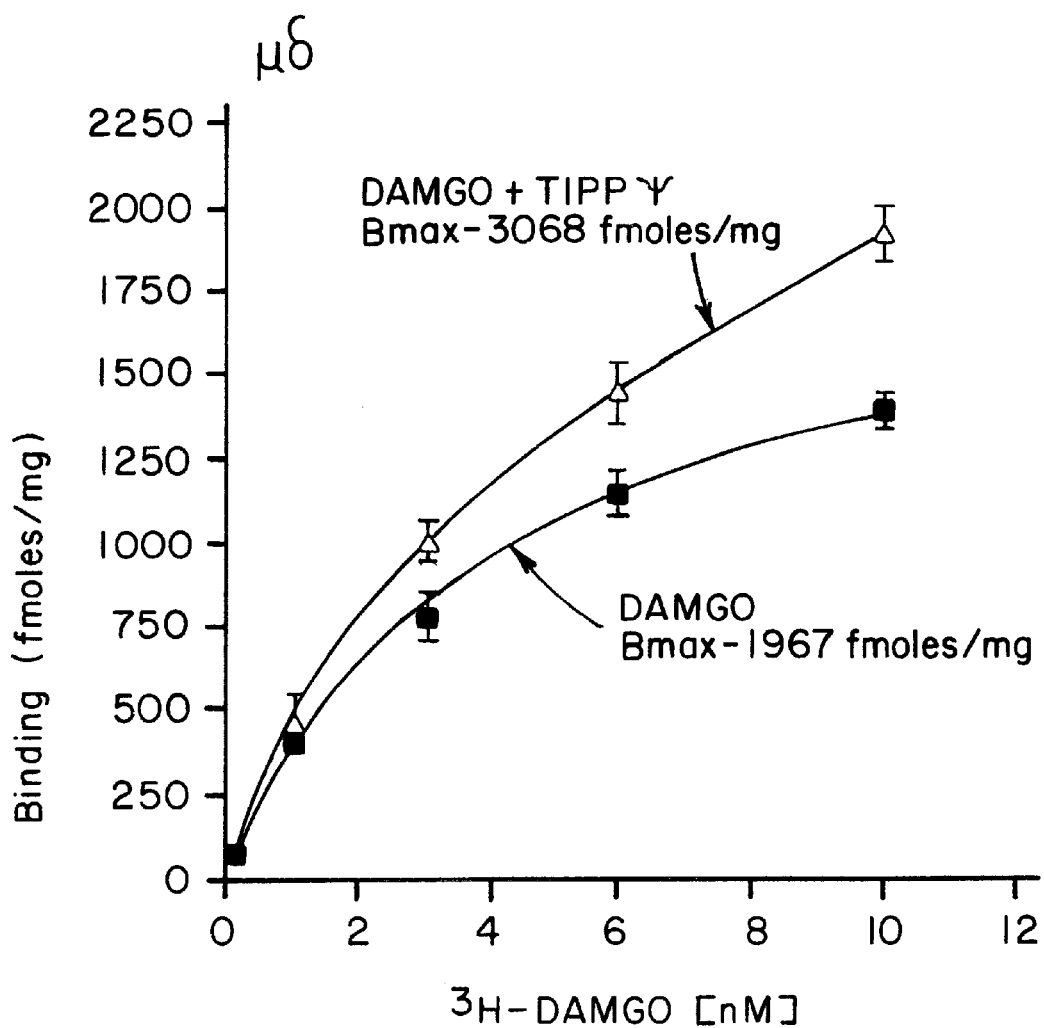
FIGS. 6A, B, C, and D. Ligand binding properties of whole cells co-expressing mu and delta receptors. Binding of a radiolabeled mu-agonist, $^3$H-DAMGO, examined in the absence or presence of a delta-antagonist, 10 nM TIPPΨ, in cells exogenously expressing mu and delta receptors (A) or in SK-N-SH neuroblastoma cells that endogenously express mu and delta receptors (B). In the presence of 10 nM TIPPΨ, a significant (about 50%) increase in the number of $^3$H-DAMGO binding sites is observed. Binding of a radiolabeled mu-agonist, $^3$H-DAMGO, examined in the absence or presence of two subtype delta selective agonists, deltorphin II (C) and DPDPE (D). The increase in the population of receptors is seen only in the presence of deltorphin II and not in the presence of DPDPE. Data in panels A–D represent mean±SEM from 3–5 independent experiments.
Figure 6B:
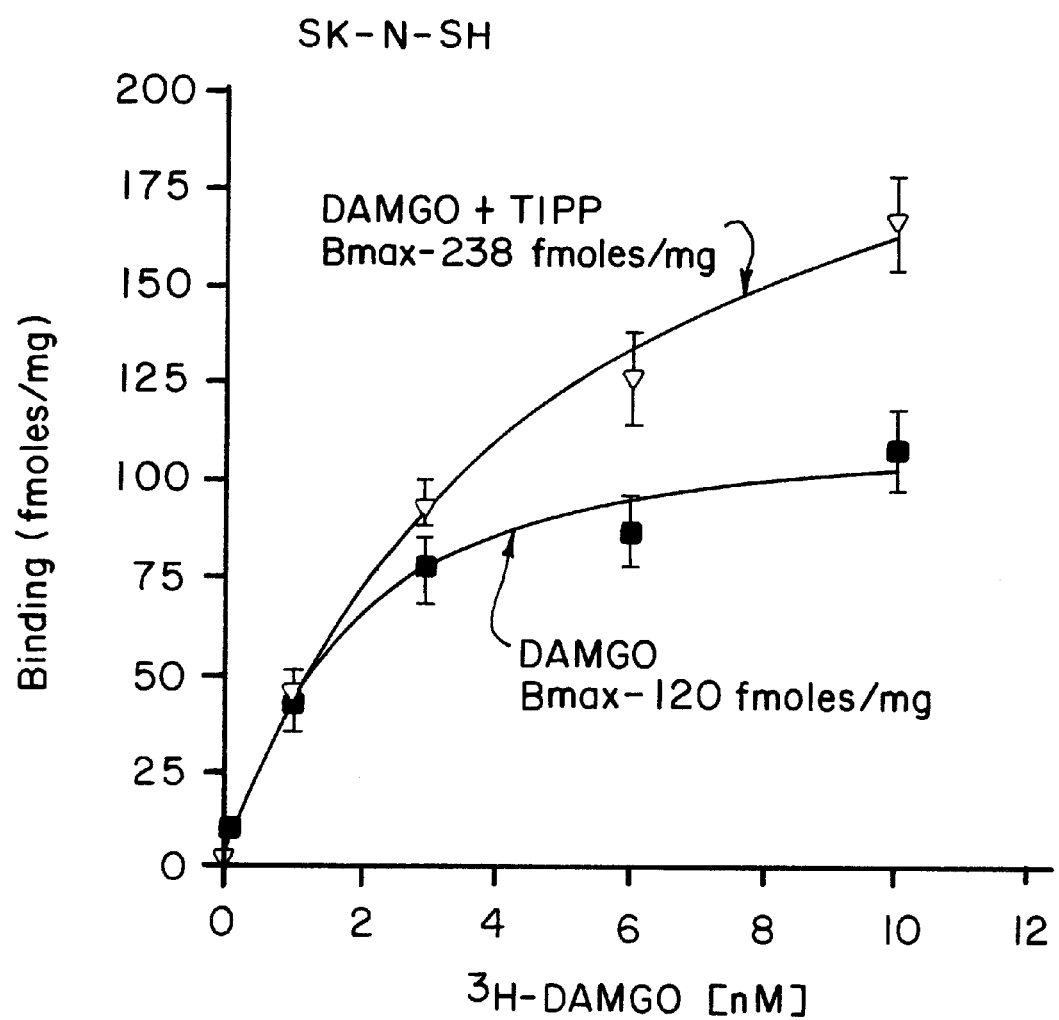
Figure 6C:
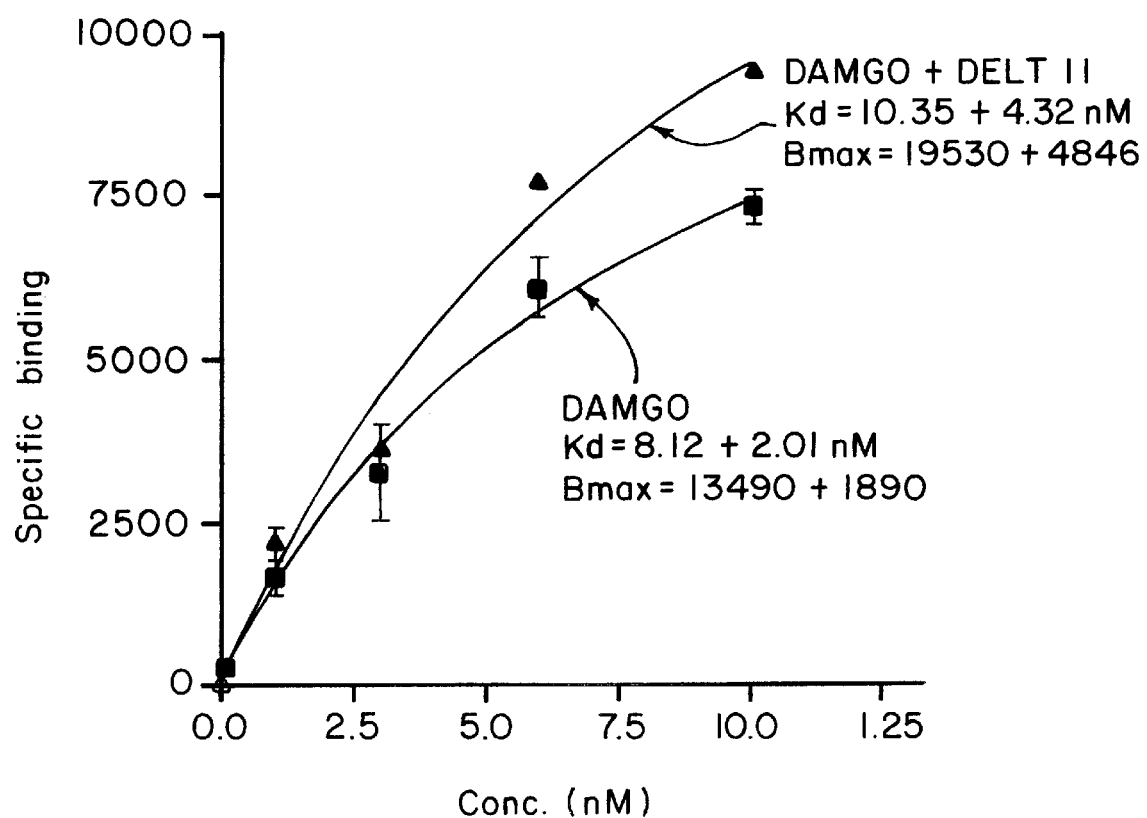
Figure 6D:
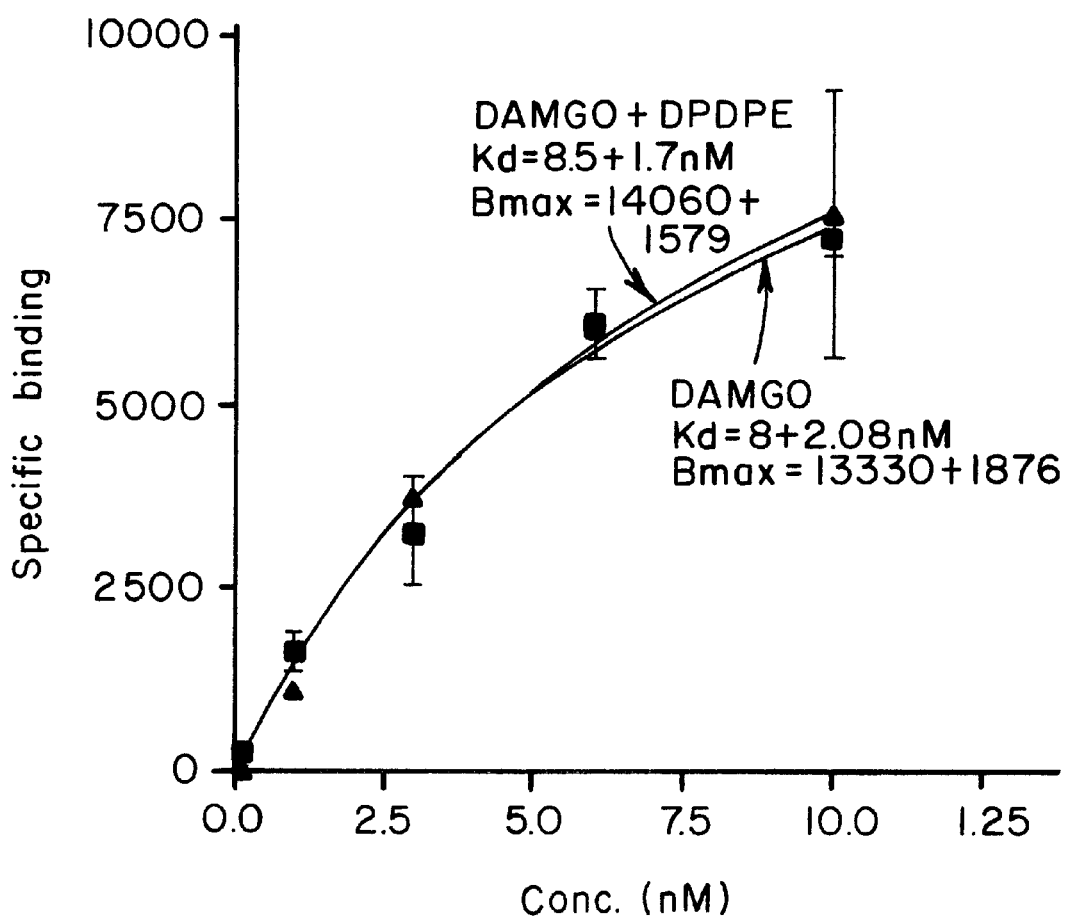

In order to explore if heterodimerization affects the ligand binding properties, a competitive ligand binding assay was performed using a non-selective opioid antagonist, [$^3$H]-diprenorphine, that binds both receptor types with equally high affinity. The ability of delta-selective antagonist TIPPΨ to modulate the affinity of a mu-selective antagonist CTOP was examined in cells expressing mu and delta receptors. CTOP was able to compete for [$^3$H]-diprenorphine with high affinity (FIG. 5). Interestingly, when the ability of CTOP to compete [$^3$H]-diprenorphine in the presence of 1 nM TIPPΨ was examined, an additional super high affinity was revealed (FIG. 5). This super high affinity site was not seen in cells expressing mu receptors alone (not shown). These results strongly support the notion that heterodimerization induces synergistic interaction between receptors resulting in the exposure of a novel binding site with increased affinity.

The mu-delta heterodimers were further characterized in cells co-expressing mu and delta receptors and in SK-N-SH neuroblastoma cells (that endogenously express mu and delta receptors) (FIG. 6). Binding of a radiolabeled mu-agonist to whole cells was examined in the absence or presence of a delta-antagonist, TIPPΨ. The number of $^3$H-DAMGO binding sites is substantially increased (by about 50%) in the presence of 10 nM TIPPΨ in both cell lines (FIGS. 6A, B); this increase was not seen in cells expressing only mu receptors (not shown). These results suggest that a population of mu receptors is able to bind the mu agonist only upon treating the cells with the delta antagonist. In order to examine if this population is uncovered by agonists of the delta receptors, two subtype selective agonists, DPDPE (delta-1) and deltorphin II (delta-2) were used. The increase in the population of receptors was seen only in the presence of deltorphin II and not in the presence of DPDPE (FIGS. 6C, D); the increase with deltorphin is not seen with cells expressing mu receptors alone (not shown). The properties of these heterodimers parallel that of the properties reported for the delta-2 receptor subtype suggesting that the mu-delta heterodimer represents the hitherto elusive delta-2 subtype of opioid receptors.

The ability of a combination of ligand to potentiate effector functions was examined using the phosphorylated MAPK assay (Jordan and Devi, DNA and Cell Biol., 19:19–27, 2000). There is a significant increase in the DAMGO-induced MAPK phosphorylation by 10 nM TIPPΨ suggesting that the mu-delta heterodimer represents a functional receptor, and delta antagonist is able to potentiate mu agonist function.

Taken together, these results support the thesis that the interaction between mu and delta receptor leading to heterodimerization is the basis for previously reported cross-talk between these two receptors.

Discussion

We have provided biochemical and functional evidence for mu-delta opioid receptor heterodimerization. By selectively co-expressing two opioid receptor types in cells lacking opiate binding, we have observed the generation of a mu-delta heterodimer. Examination of the ligand binding properties shows the presence of a novel binding site in heterologous cells expressing mu and delta receptors as well as in neuroblastoma cells that contain endogenous receptors. This novel high affinity binding site is revealed by the synergistic binding of receptor type selective ligands. Morphine and other opiates bind this site with very high affinity ($K_i=10^{-13}$M). Thus, receptor heterodimerization forms the molecular basis for the generation of this very high affinity opiate receptor. This has enormous clinical significance as well as high impact on drug abuse research since it represents another mechanism that could modulate receptor function and provides a new strategy for the development of novel therapies.

Example 3

Heterodimerization of Kappa and Delta Opioid Receptors with Catecholamine Receptors This example presents data that show that kappa receptors heterodimerize with $β_2$-adrenergic and D2 dopamine receptors, and that delta receptors heterodimerize with mu opioid, $β_2$-adrenergic, and D2 dopamine receptors.

Materials and Methods

Generation of cell lines expressing opioid receptors.

The rat kappa opioid receptor cDNA, mouse delta, or mouse mu receptor cDNA were tagged with either a FLAG epitope or a myc epitope by an overlapping extension polymerase chain reaction and subcloned into pCDNA-3 (Invitrogen). Human FLAG-tagged $β_2$-adrenergic receptor or D2 dopamine receptor cDNAs were obtained from Dr. J. Jaritch (Columbia University) and HA-tagged $α_2$-adrenergic receptors were obtained from Dr. L. Limberd (Vanderbilt University). Cells expressing delta plus mu, kappa plus $β_2$, kappa plus D2, delta plus $β_2$ and delta plus D2 receptors were generated by transfecting either HEK293 or COS cells (for transient expression), as described Example 1, Materials and Methods.

Dimerization, Immunoprecipitation and Western blotting.

Cross-lining, SDS-PAGE and Western blotting were carried out on whole cell lysates or membranes essentially as described (Cvejic and Devi, supra and Example 2) except that cells were lysed at room temperature for 60 minutes. For immunoprecipitation 1–2 µg of proteins were incubated overnight at 4° C. with either 0.5 µg of monoclonal anti-FLAG antibody (Sigma), 0.5 µg of polyclonal anti-myc antibody (Santa Cruz) or monoclonal anti-HA antibody (BABCO). Immunocomplexes were isolated by incubation with 20 µg of protein A-Sepharose followed by centrifugation and analyzed by Western blotting as described (Cvejic and Devi, supra).

Results

Figure 7C:
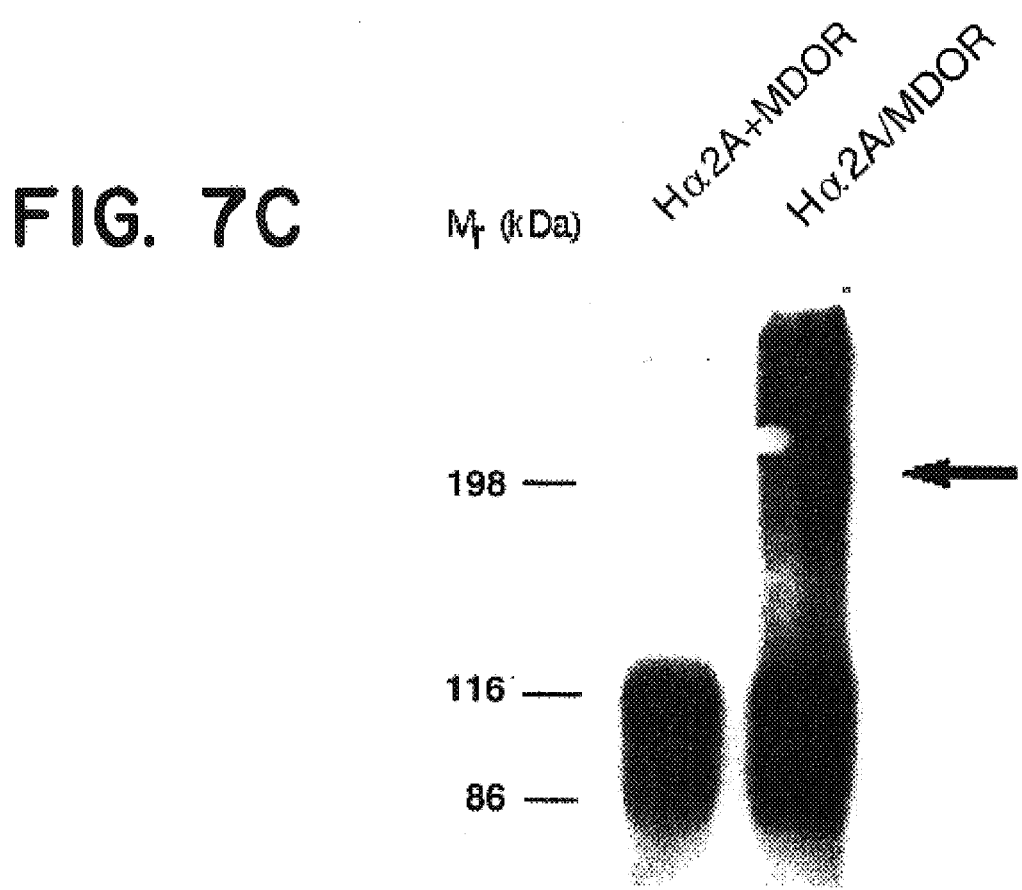
FIGS. 7A, B, and C. Delta opioid receptors interact with $β_2$- adrenergic receptors (A), with D2 dopamine receptors (B), or with $α_2$A-adrenergic receptors (C) to form heterodimers. A. Western blotting (left and right panels) and immunoprecipitation (middle panel) of cell lysates from mixed HEK-293 cells individually expressing either FLAG-$β_2$-adrenergic receptors or myc-delta receptors, or cells co-expressing FLAG-$β_2$-adrenergic receptors and myc-delta receptors was carried out using either anti-FLAG or anti-myc antibodies. Western blotting of anti-myc-precipitated immunocomplexes with anti-FLAG antibodies shows delta-$β_2$ heterodimers only in cells co-expressing both FLAG-$β_2$ and myc-delta receptors. B. Western blotting (left and right panels) and immunoprecipitation (middle panel) of cell lysates from mixed HEK-293 cells individually expressing either FLAG-D2 dopamine receptors or myc-delta receptors, or cells co-expressing FLAG-D2 dopamine receptors and myc-delta receptors was carried out using either anti-FLAG or anti-myc antibodies. Western blotting of anti-myc-precipitated immunocomplexes with anti-FLAG antibodies shows delta-D2 heterodimers only in cells co-expressing both FLAG-D2 and myc-delta receptors. C Western blotting following the immunoprecipitation of cell lysates from mixed HEK-293 cells individually expressing either HA-$α_2$A-adrenergic receptors or myc-delta receptors (left panel), or from cells co-expressing HA-$α_2$A-adrenergic receptors and myc-delta receptors (right panel). Western blotting of anti-HA-precipitated immunocomplexes was performed using anti-myc antibodies and shows delta-$α_2$A heterodimers only in cells co-expressing both HA-$β_2$A-adrenergic receptors and myc-delta receptors.
Figure 7A:
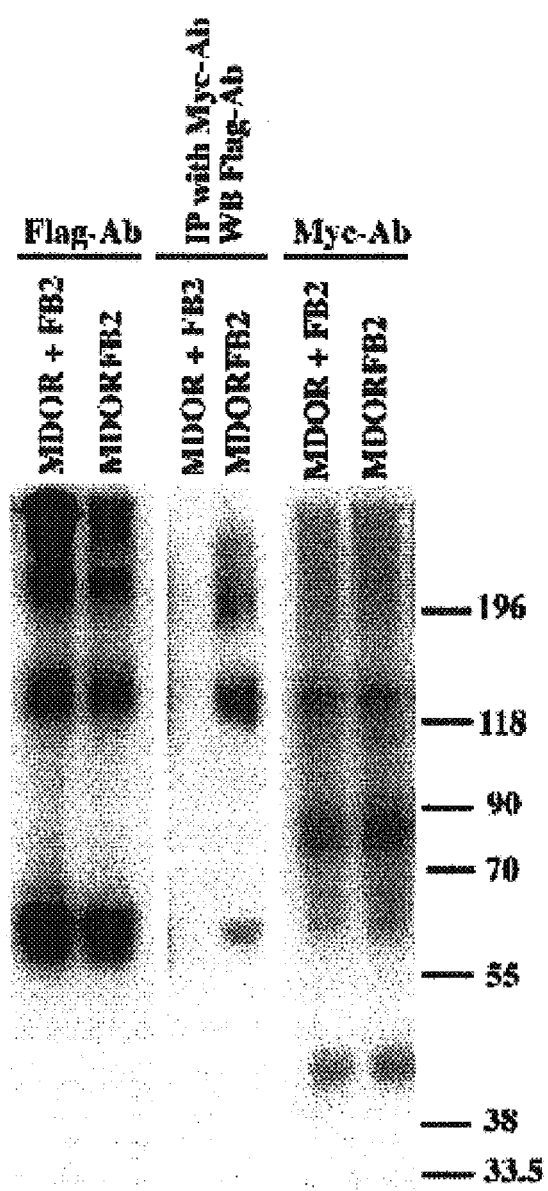
Figure 7B:
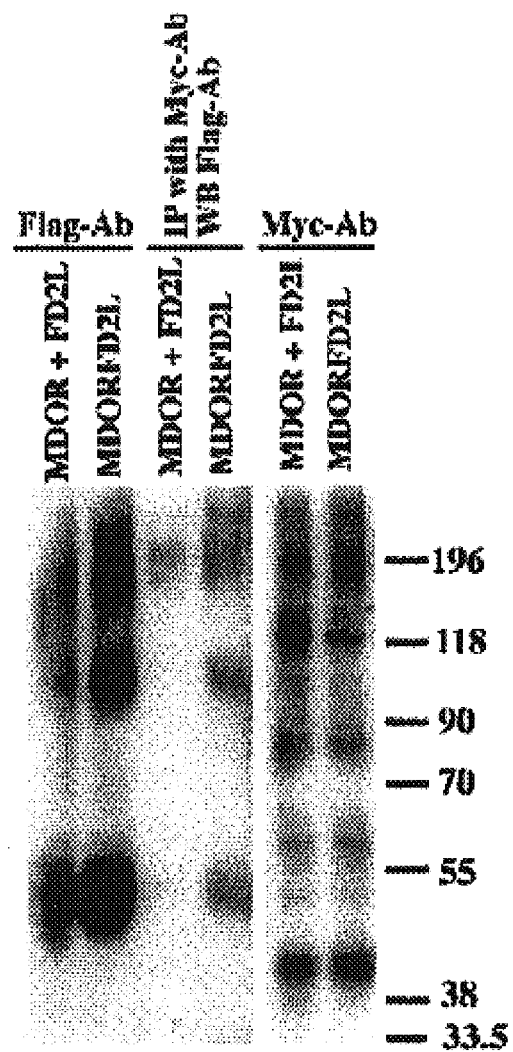

Kappa receptors heterodimerize with $\beta_2$-adrenergic receptor and D2 dopamine receptor. Also, delta receptors heterodimerize with mu opioid, $\beta_2$-adrenergic, D2 dopamine receptors and $\alpha_2$A-adrenergic receptors. Recently we have also found that mu opioid receptors heterodimerize with $\alpha_2$A-adrenergic receptors. These heterodimers are observed only in lysate from cells co-expressing the two receptors and not in the lysate from a mixture of cells individually expressing these receptors (FIGS. 4, 7).

Example 4
Investigation of GPCR Heterodimerization and the Effect of Agonist/Antagonist Binding Using the BRET Technique General Methodology.

The Bioluminescence Resonance Energy Transfer (BRET) technique measures the transfer of energy between a luminescent donor (e.g., luciferase) and a fluorescent acceptor (e.g., yellow fluorescent protein, YFP). When luciferase is used as a luminescent donor, the catalytic degradation of its substrate, coelenterazine, leads to the release of the bioluminescent energy which can excite YFP. The resulting fluorescence emission is used as a measure of physical association between the two proteins. Since the Forster energy transfer occurs only when the distance between the donor and acceptor is less than 100Å, this method is ideally suited to examine protein-protein interactions (see, e.g., Xu et al., Proc. Natl. Acad. Sci. USA, 96:151–156, 1999; Angers et al., Proc. Natl. Acad. Sci. USA, 97:3684–3689, 2000).

According to the present invention, BRET is used to examine heterodimerization between opioid receptor types and between opioid and catecholamine receptors (see, e.g., Angers et al., supra; Angers et al. successfully applied the BRET technique to examine homo-dimerization of $\beta_2$-adrenergic receptor). In addition, BRET is used to investigate the effect of various candidate compounds as well as known receptor agonists/antagonists (or a combination of agonists/antagonists) on the level of dimers.

Constructs.

Fusion proteins containing delta or mu opioid receptors fused at their C-termini to luciferase (for delta-Rluc and mu-Rluc) or YFP (for delta-YEP and mu-YFP) were prepared. Fusion proteins were constructed by PCR-amplification of a complete coding sequence of the delta or mu receptor without their stop codon. The amplification was performed using primers harboring a unique NheI restriction site. The resulting amplified fragments were subcloned in-frame into the NheI site of the YFP expression vector (Clontech) or pRL-CMV-Rluc expression vector (Promega). A similar strategy can be used to generate fusion proteins of various opioid and catecholamine receptors.

Assays.

For the BRET assay, HEK-293 cells are co-transfected with delta-Rluc and mu-YFP fusion proteins. In a parallel assay, cells are co-transfected with delta-YFP and mu-Rluc. Cells are collected after 48 hours and incubated with 5 µM coelenterazine (Molecular Probes). Light emission spectra are acquired from 400 nm to 600 nm using a spectrofluorimeter. The signals at 440–500 nm (luciferase emission) and 510–590 nm (YFP emission) are integrated. The ratio of the integrated emission values is used as a measure of dimerization.

Compound screens.

To study the effect of various candidate compounds and known agonists/antagonists on receptor dimerization, the transfected cells are incubated with a test substance prior to treatment with 5 µM coelenterazine. Control cells are incubated without a test substance.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values are approximate, and are provided for description.

All patents, patent applications, publications, and other materials cited herein are hereby incorporated herein by reference in their entireties.

We claim:

1. An isolated heterodimeric receptor, wherein said receptor comprises first opioid receptor subunit and a second G-protein coupled receptor (GPCR) subunit, and wherein both receptor subunits are expressed in the same cell.

2. The heterodimeric receptor of claim 1, wherein the second receptor subunit is an opioid receptor protein that is distinct from the first opioid receptor subunit protein.

3. The heterodimeric receptor of claim 1, wherein the second receptor subunit is a dopamine receptor protein.

4. The heterodimeric receptor of claim 1, wherein the second receptor subunit is an adrenergic receptor protein.

5. The heterodimeric receptor of claim 1, wherein the second receptor subunit is a chemokine receptor protein.

6. The heterodimeric receptor of claim 1, wherein the opioid receptor subunit is a delta opioid receptor protein and the second receptor subunit is selected from the group consisting of kappa opioid receptor protein, mu opioid receptor protein, D2 dopamine receptor protein, and β2-adrenergic receptor protein.

7. The heterodimeric receptor of claim 1, wherein the opioid receptor subunit is a kappa opioid receptor protein and the second receptor subunit is selected from the group consisting of delta opioid receptor protein, D2 dopamine receptor protein, α2-adrenergic receptor protein, β2-adrenergic receptor protein, CCR5 protein, and CXCR4 protein.

8. The heterodimeric receptor of claim 1, wherein the opioid receptor subunit is a mu opioid receptor protein and the second receptor subunit is selected from the group consisting of delta opioid receptor protein and α2-adrenergic receptor protein.

9. The heterodimeric receptor of claim 1, wherein the opioid receptor subunit is a fusion protein comprising a sequence of a functional opioid receptor protein and a tag sequence.

10. The heterodimeric receptor of claim 1, wherein the second receptor subunit is a fusion protein comprising a sequence of a functional second receptor protein and a tag sequence.

11. A recombinant host cell that expresses a functional heterodimeric receptor, wherein said receptor comprises an opioid receptor subunit expressed from an expression vector introduced into the host cell, and a second G-protein coupled receptor (GPCR) subunit expressed from an expression vector introduced into the same host cell, wherein the host cell does not endogenously express the receptor subunits.

12. The host cell of claim 11, wherein the second receptor subunit is a different opioid receptor protein or a covalently associated opioid receptor protein.

13. The host cell of claim 11, wherein the second receptor subunit is a dopamine receptor protein.

14. The host cell of claim 11, wherein the second receptor subunit is an adrenergic receptor protein.

15. The host cell of claim 11, wherein the second receptor subunit is a chemokine receptor protein.

16. The host cell of claim 11, wherein the opioid receptor subunit is a delta opioid receptor protein and the second receptor subunit is selected from the group consisting of kappa opioid receptor protein, mu opioid receptor protein, D2 dopamine receptor protein, and β2-adrenergic receptor protein.

17. The host cell of claim 11, wherein the opioid receptor subunit is a kappa opioid receptor protein and the second receptor subunit is selected from the group consisting of delta opioid receptor protein, D2 dopamine receptor protein, α2-adrenergic receptor protein, β2-adrenergic receptor protein, CCR5 protein, and CXCR4 protein.

18. The host cell of claim 11, wherein the opioid receptor subunit is a mu opioid receptor protein and the second receptor subunit is selected from the group consisting of delta opioid receptor protein and α2-adrenergic receptor protein.

19. A method of screening for a compound that modulates a property of a heterodimeric receptor, wherein said receptor comprises an opioid receptor subunit and a second G-protein coupled receptor (GPCR) subunit, wherein both receptor subunits are heterologously expressed in a host cell, which method comprises observing a change in a property of the heterodimeric receptor contacted with a candidate compound.

20. The method according to claim 19, wherein the heterodimeric receptor property is trafficking of the heterodimeric receptor.

21. The method according to claim 19, wherein the heterodimeric receptor property is binding affinity for a ligand.

22. The method according to claim 19, wherein the heterodimeric receptor property is activation of a signal transduction pathway.

23. The method according to claim 22, wherein the signal transduction pathway is selected from the group consisting of cAMP production and MAPK phosphorylation.

* * * * *